US008877899B2

(12) United States Patent
Rojkjaer et al.

(10) Patent No.: US 8,877,899 B2
(45) Date of Patent: Nov. 4, 2014

(54) ANTI-CD38 ANTIBODY AND LENALIDOMIDE OR BORTEZOMIB FOR THE TREATMENT OF MULTIPE MYELOMA AND NHL

(75) Inventors: Lisa Rojkjaer, Hedingen (CH); Rainer Boxhammer, Aying (DE); Jan Endell, Munich (DE); Mark Winderlich, Munich (DE); Christofer Samuelsson, Holzkirchen (DE)

(73) Assignee: Morphosys AG, Martinsried/Planegg (DE)

(*) Notice: Subject to any disclaimer, the term of this patent is extended or adjusted under 35 U.S.C. 154(b) by 0 days.

(21) Appl. No.: 13/825,325

(22) PCT Filed: Sep. 26, 2011

(86) PCT No.: PCT/EP2011/066648
§ 371 (c)(1),
(2), (4) Date: Mar. 21, 2013

(87) PCT Pub. No.: WO2012/041800
PCT Pub. Date: Apr. 5, 2012

(65) Prior Publication Data
US 2013/0302318 A1 Nov. 14, 2013

Related U.S. Application Data

(60) Provisional application No. 61/386,619, filed on Sep. 27, 2010, provisional application No. 61/437,696, filed on Jan. 31, 2011, provisional application No. 61/468,607, filed on Mar. 29, 2011, provisional application No. 61/486,814, filed on May 17, 2011.

(30) Foreign Application Priority Data

Sep. 27, 2010 (EP) .................................. 10180485

(51) Int. Cl.
| | | |
|---|---|---|
| *A61K 39/395* | (2006.01) | |
| *C07K 16/28* | (2006.01) | |
| *C07K 16/30* | (2006.01) | |
| *A61K 31/69* | (2006.01) | |
| *A61K 45/06* | (2006.01) | |
| *A61K 38/07* | (2006.01) | |
| *A61K 38/05* | (2006.01) | |
| *A61K 31/454* | (2006.01) | |
| *A61K 39/00* | (2006.01) | |

(52) U.S. Cl.
CPC ..... *A61K 39/39558* (2013.01); *C07K 2317/565* (2013.01); *C07K 16/28* (2013.01); *C07K 16/3061* (2013.01); *C07K 2317/56* (2013.01); *A61K 31/69* (2013.01); *C07K 16/2896* (2013.01); *A61K 2039/505* (2013.01); *A61K 45/06* (2013.01); *A61K 38/07* (2013.01); *C07K 2317/73* (2013.01); *A61K 38/05* (2013.01); *A61K 31/454* (2013.01)
USPC .................. 530/387.3; 530/387.7; 424/138.1

(58) Field of Classification Search
None
See application file for complete search history.

(56) References Cited

U.S. PATENT DOCUMENTS

| | | | |
|---|---|---|---|
| 7,829,673 | B2 | 11/2010 | De Weers |
| 8,088,896 | B2 | 1/2012 | Tesar |
| 8,263,746 | B2 | 9/2012 | Tesar |
| 2002/0164788 | A1 | 11/2002 | Ellis |
| 2009/0123950 | A1 | 5/2009 | Tesar |

FOREIGN PATENT DOCUMENTS

| | | |
|---|---|---|
| WO | 9962526 | 12/1999 |
| WO | 0040265 | 7/2000 |
| WO | 0206347 | 1/2001 |
| WO | 2005103083 | 11/2005 |
| WO | 2006099875 | 9/2006 |
| WO | 2006125640 | 11/2006 |
| WO | 2007042309 | 4/2007 |
| WO | 2008037257 | 4/2008 |
| WO | 2008047242 | 4/2008 |
| WO | 2010061357 | 6/2010 |
| WO | 2010061358 | 6/2010 |
| WO | 2010061359 | 6/2010 |
| WO | 2010061360 | 6/2010 |
| WO | 2012076663 | 6/2012 |
| WO | 2012092612 | 7/2012 |
| WO | 2012092616 | 7/2012 |

OTHER PUBLICATIONS

Wiernik Peter H: "Treatment of hematologic neoplasms with new immunomodulatory drugs (IMiDs)." Current Treatment Options in Oncology Apr. 2009 LNKD-PUBMED: 19016330, vol. 10, No. 1-2, Apr. 2009.
Stevenson G.T: "CD38 as a therapeutic target", Molecular Medicine 200611 US LNKD-DOI:10.2119/2006-00082.Stevenson, vol. 12, No. 11-12, Nov. 2006, pp. 345-346.
Richards Tiffany et al.: "Advances in treatment for relapses and refractory multiple myeloma", Medical Oncology (Totowa), vol. 27, NO. Suppl. 1, Jun. 2010, pp. 25-42.
Lapalombella Rosa, et al: "Lenalidomide down-regulates the CD20 antigen and antagonizes direct and antibody-dependent cellular cytotoxicity of rituximab on primary chronic lymphocytic leukemia cells", Blood, American Society of Hematology, US, vol. 112, No. 13, Dec. 15, 2008, pp. 5180-5189.
Ghosh Nilanjan, et al: "Bortezomib and Thalidomide, a steroid free regimen in newly diagnosed patients with multiple myeloma", Blood, vol. 114, No. 22, Nov. 2009, p. 1119.
Van Der Veer Michael S. et al.: "Towards effective immunotherapy of myeloma: enhanced elimination of myeloma cells by combination of Lenalidomide with the human CD38 monoclonal antibody daratumumab", Haematologica Feb. 2011, pp. 284-290.
Chou: "Theoretical Basis, Experimental Design, and Computerized Simulation of Synergism and Antagonism in Drug Combination Studies", Pharmacological Reviews, 2006 by the American Society for Pharmacology and Experimental Therapeutics 60308/3141065, Pharmacol Rev 58:621-681, 2006, vol. 58, No. 3.
EP10180485.4, European Search Report, 2011.
International Preliminary Report on Patentability dated Jan. 27, 2012 including the Written Opinion for PCT Application No. PCT/EP2011/06648.
PCT/EP2011/066648 IPEA dated Apr. 11, 2013.

*Primary Examiner* — Sheela J Huff
(74) *Attorney, Agent, or Firm* — Jones Day

(57) ABSTRACT

The present disclosure describes a pharmaceutical combination of an anti-CD38 antibody and lenalidomide and a pharmaceutical combination of an anti-CD38 antibody and bortezomib.

19 Claims, 20 Drawing Sheets

CD38 upregulation on AMO-1 cells by Lenalidomide

Influence of Lenalidomide Alone on Cell Proliferation

PBMCs and AMO-1 cells treated with lenalidomide prior to treatment with MOR202.

PBMCs alone were treated with lenalidomide prior to treatment with MOR202.

PBMCs and NCI-H929 cells were treated with lenalidomide prior to treatment with MOR202.

PBMCs alone were treated with lenalidomide prior to treatment with MOR202.

Effect of MOR202 and Velcade on ADCC in NCI-H929 Cells

**Figure 10
Effect of MOR202 and Velcade on ADCC in LP-1 Cells**
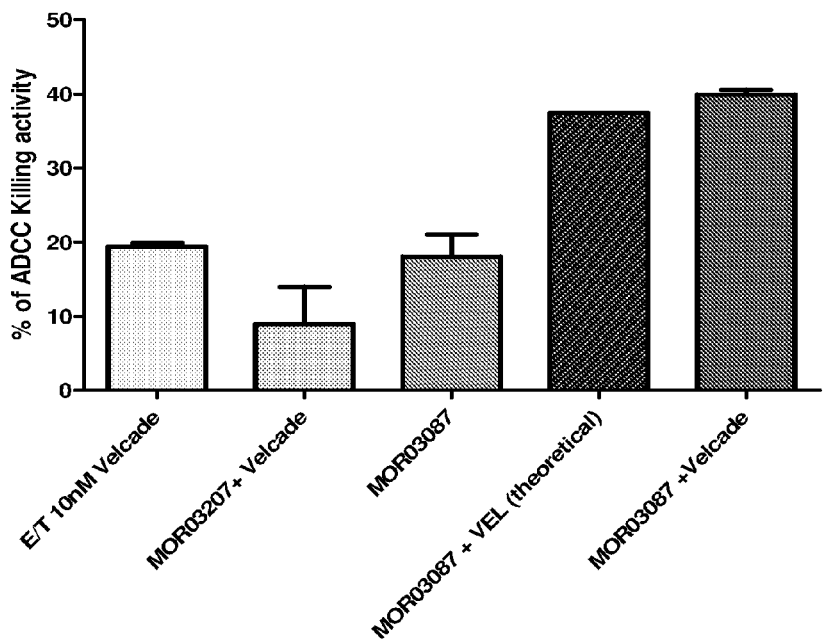
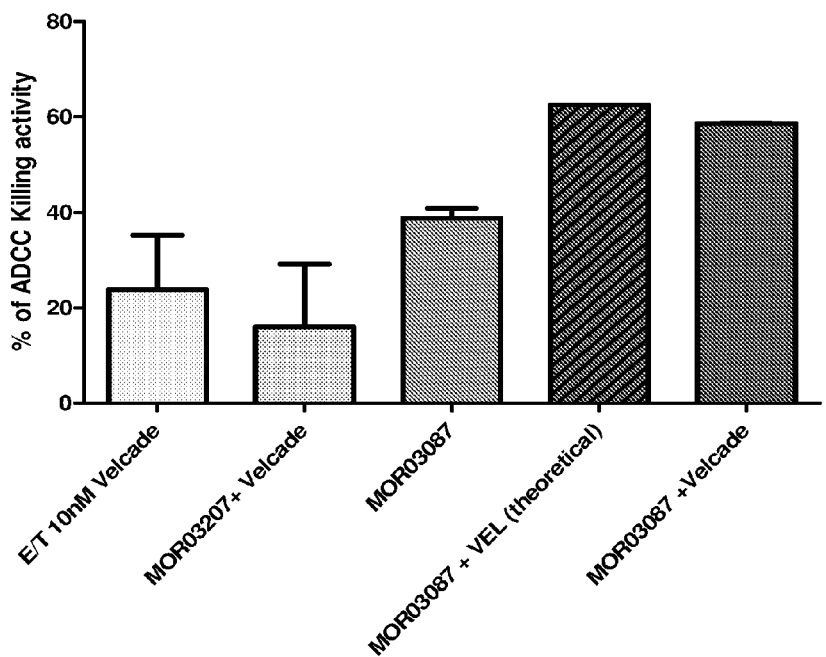

Figure 11

The amino acid sequence of the MOR202 Variable Heavy Domain is:

QVQLVESGGGLVQPGGSLRLSCAASGFTFSSYYMNWVRQAPGKGLEWVSGISGDPS
NTYYADSVKGRFTISRDNSKNTLYLQMNSLRAEDTAVYYCARDLPLVYTGFAYWGQGTLVTV
SS (SEQ ID NO: 10)

The amino acid sequence of the MOR202 Variable Light Domain is:

DIELTQPPSVSVAPGQTARISCSGDNLRHYYVYWYQQKPGQAPVLVIYGDSKRPSGIP
ERFSGSNSGNTATLTISGTQAEDEADYYCQTYTGGASLVFGGGTKLTVLGQ (SEQ ID NO: 11)

The amino acid sequence of the MOR202 HCDR1 as defined by an internal nomenclature is: GFTFSSYYMN (SEQ ID NO: 1)

The amino acid sequence of the MOR202 HCDR1 as defined by Kabat is: SYYMN (SEQ ID NO: 14)

The amino acid sequence of the MOR202 HCDR2 as defined by Kabat is: GISGDPSNTYYADSVKG (SEQ ID NO: 2)

The amino acid sequence of the MOR202 HCDR3 as defined by Kabat is: DLPLVYTGFAY (SEQ ID NO: 3)

The amino acid sequence of the MOR202 LCDR1 as defined by Kabat is: SGDNLRHYYVY (SEQ ID NO: 4)

The amino acid sequence of the MOR202 LCDR2 as defined by Kabat is: GDSKRPS (SEQ ID NO: 5)

The amino acid sequence of the MOR202 LCDR3 as defined by Kabat is: QTYTGGAS (SEQ ID NO:6)

"Best Fit" curve for the combination of MOR202 and lenalidomide in the mediation of ADCC in AMO-1 cells.

| MOR202 µg/ml | Effect (%dead) |
|---|---|
| 0.011574 | 46.000000 |
| 0.069444 | 65.000000 |
| 0.416667 | 77.000000 |
| 2.500000 | 94.000000 |

$Y=100/(1+10^{((Dm-X)*m)})$

Figure 13
Y Exp 1
| raw data | |
|---|---|
| X | Y |
| 0.012 | 0.37997 |
| 0.07 | 0.501679 |
| 0.42 | 0.643211 |
| 2.5 | 0.631401 |
| 15 | 0.59145 |
| XL fit calulations | |
|---|---|
| chart | #Ok |
| fit | #Ok |
| Dm | 0.083866 |
| m | 0.129731 |
| r^2 | 0.644434 |
| (lin. correlation ciefficient) | |
data fitted to $y=f(x)=1/(1+((Dm/x)^m))$
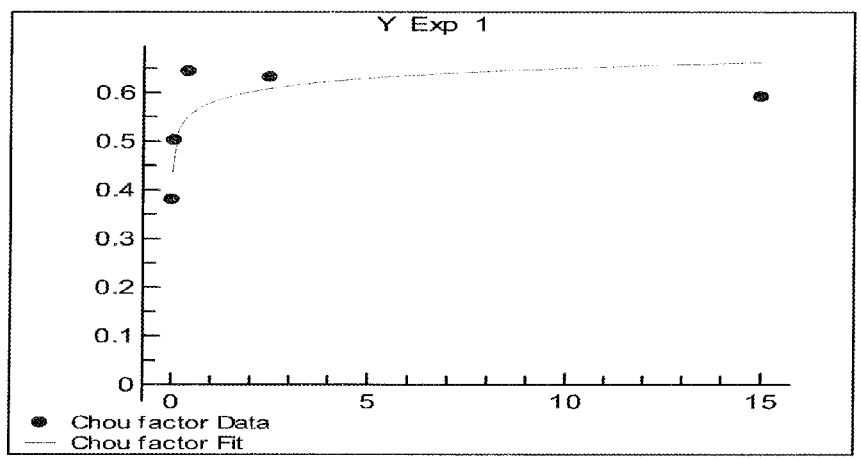
zoomed plot of data and fit
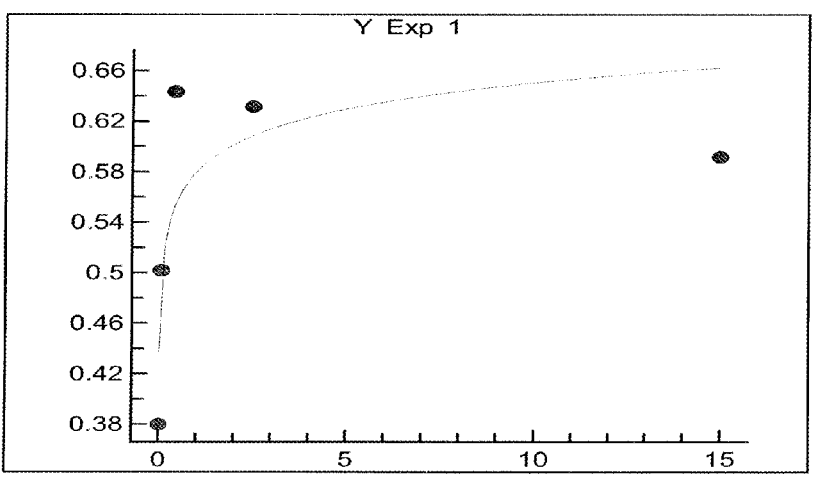

Figure 14
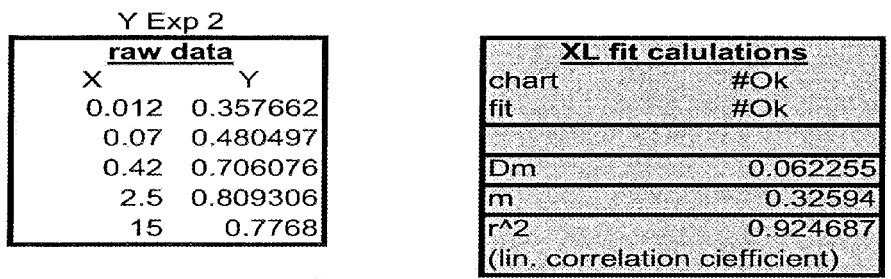
data fitted to y=f(x)=1/(1+((Dm/x)^m))
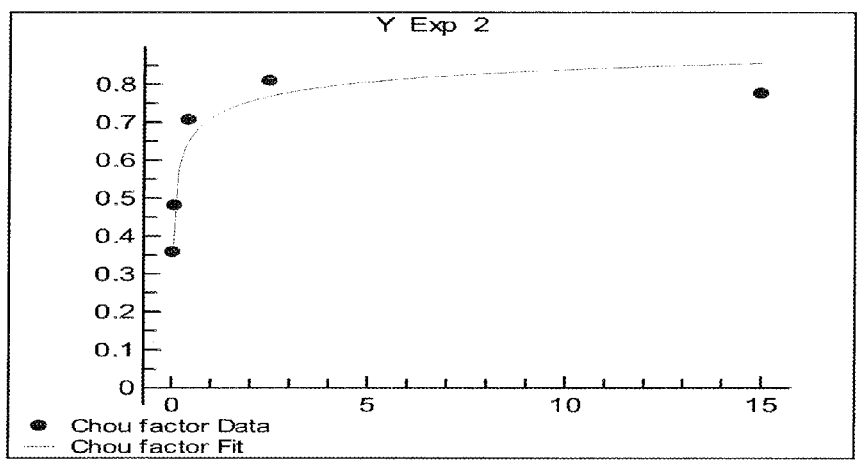
zoomed plot of data and fit
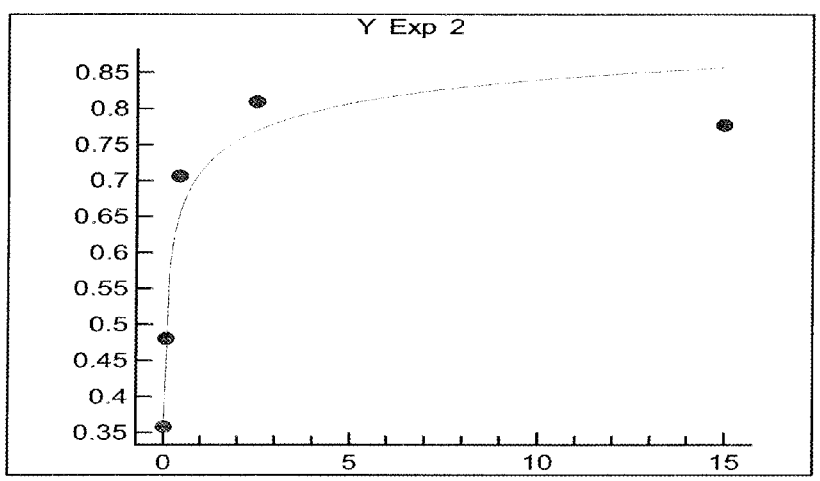

Figure 15
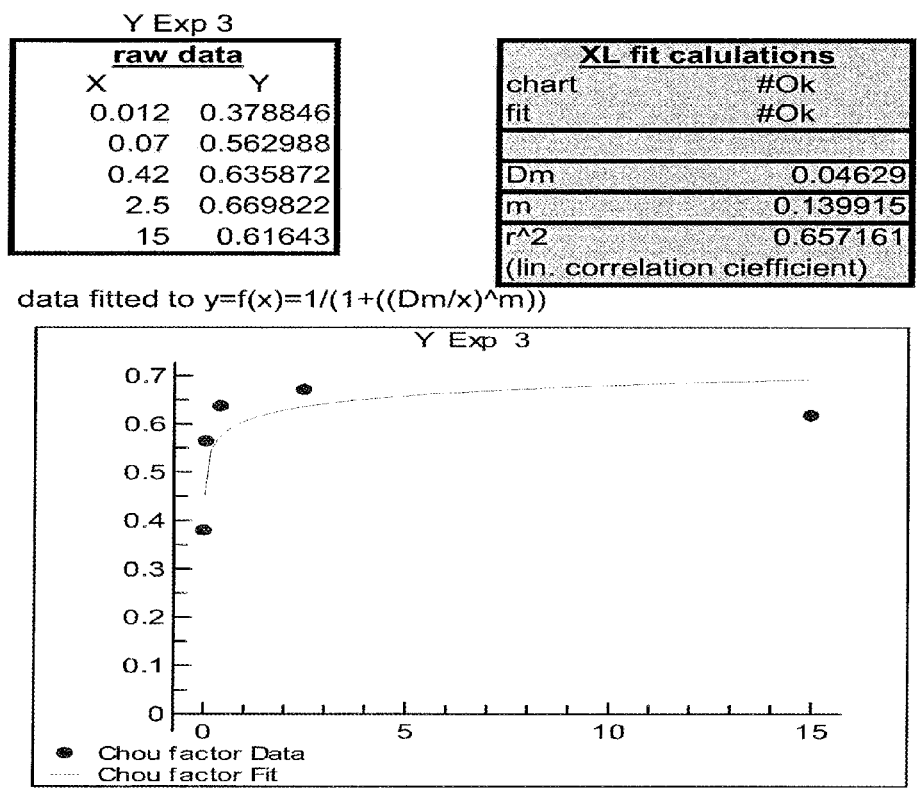
data fitted to y=f(x)=1/(1+((Dm/x)^m))
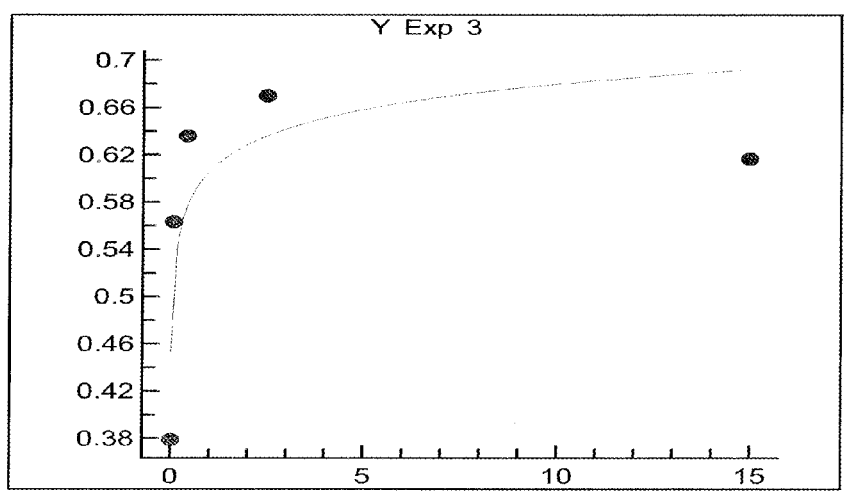

Figure 16
Y Exp 4
raw data
| X | Y |
|---|---|
| 0.012 | 0.575381 |
| 0.07 | 0.551706 |
| 0.42 | 0.797069 |
| 2.5 | 0.855131 |
| 15 | 0.824584 |
| XL fit calulations | |
|---|---|
| chart | #Ok |
| fit | #Ok |
| Dm | 0.006182 |
| m | 0.245157 |
| r^2 | 0.795756 |
| (lin. correlation ciefficient) | |
data fitted to $y=f(x)=1/(1+((Dm/x)^m))$
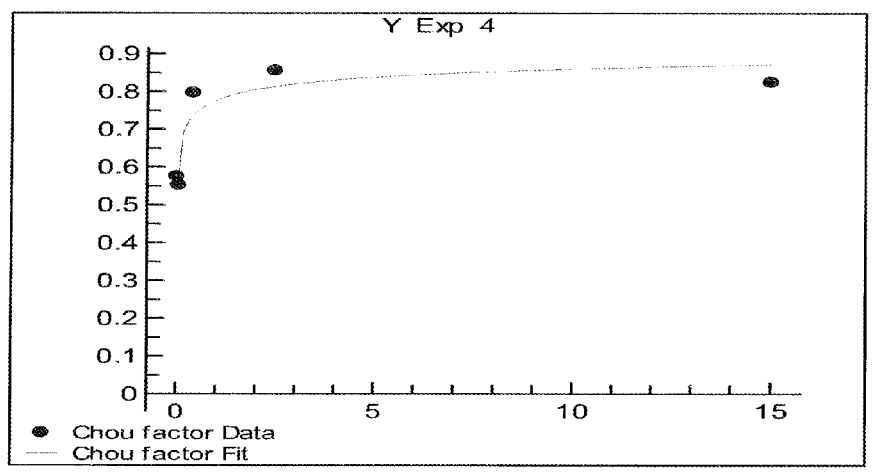
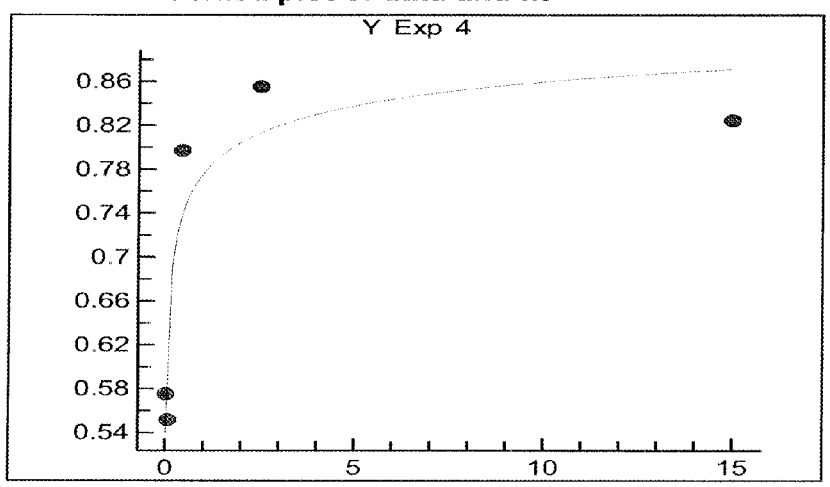
zoomed plot of data and fit

Figure 17
Y Exp 5
| raw data | |
|---|---|
| X | Y |
| 0.012 | 0.361208 |
| 0.07 | 0.486295 |
| 0.42 | 0.703533 |
| 2.5 | 0.759272 |
| 15 | 0.747995 |
| XL fit calulations | |
|---|---|
| chart | #Ok |
| fit | #Ok |
| Dm | 0.063193 |
| m | 0.278814 |
| r^2 | 0.90303 |
| (lin. correlation cieficient) | |
data fitted to y=f(x)=1/(1+((Dm/x)^m))
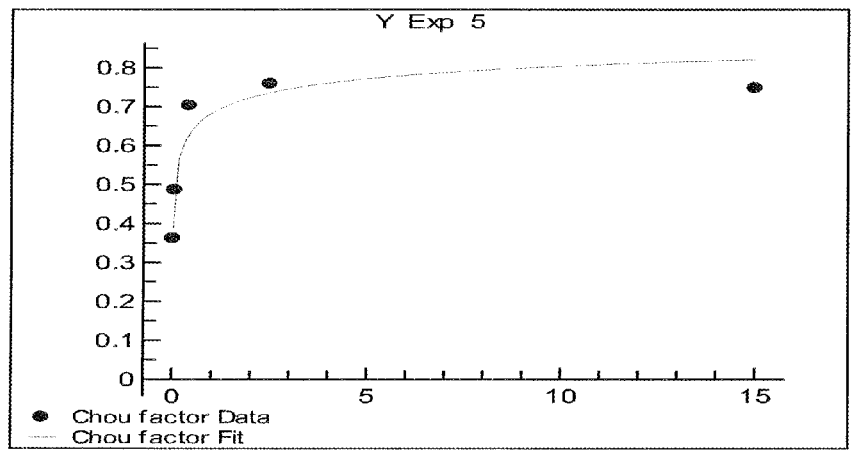
zoomed plot of data and fit
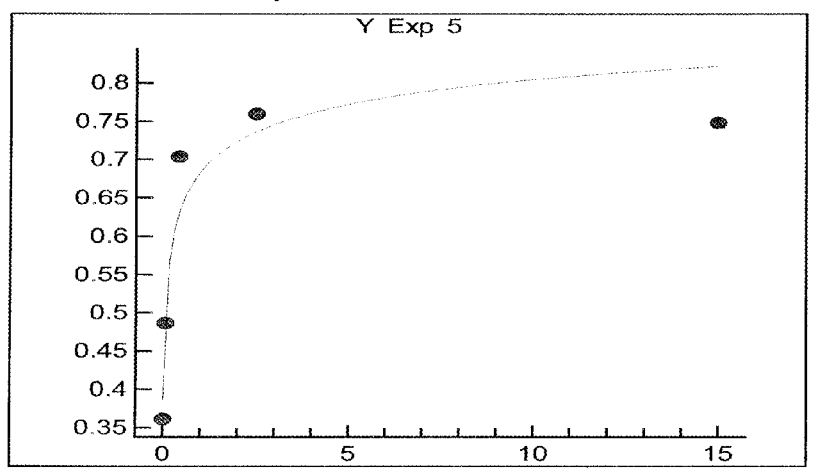

Figure 18
| Y Exp 6 raw data | |
|---|---|
| X | Y |
| 0.012 | 0.456555 |
| 0.07 | 0.649115 |
| 0.42 | 0.761269 |
| 2.5 | 0.93137 |
| 15 | 0.85444 |
| XL fit calulations | |
|---|---|
| chart | #Ok |
| fit | #Ok |
| Dm | 0.016501 |
| m | 0.379718 |
| r^2 | 0.930189 |
| (lin. correlation ciefficient) | |
data fitted to $y=f(x)=1/(1+((Dm/x)^m))$
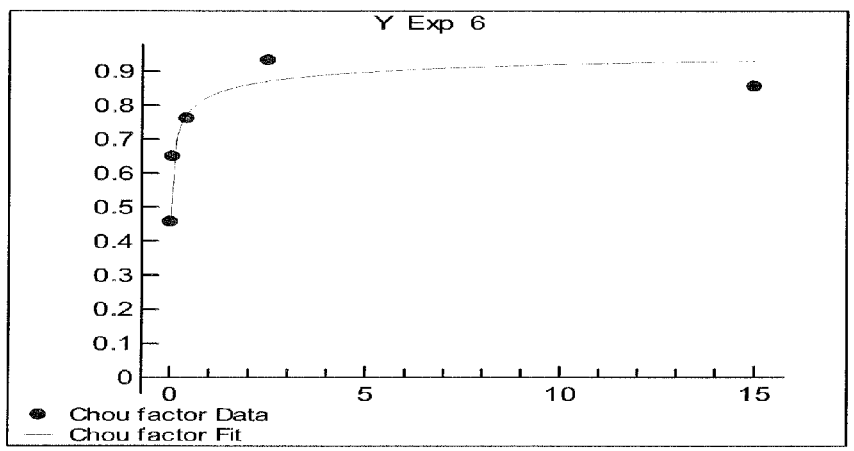
zoomed plot of data and fit
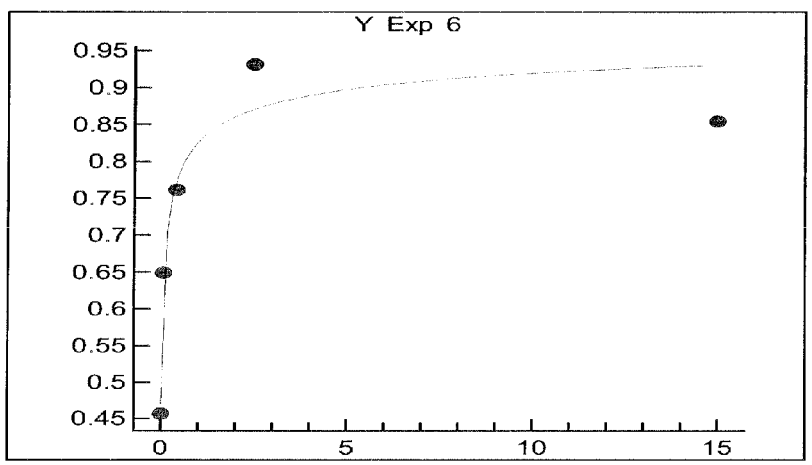

Mean Total Bone Volume +/- SEM for Each Study Group

A: LEN 50mg/kg, p.o. in 10mL/kg
B: MOR202 3 mg/kg, i.p., in 10 mL/kg
C: Vehicle Control (Ora Plus: Ora Sweet) 10mL/kg, p.o.
AB: LEN 50mg/kg p.o. in 10mL/kg + MOR202 3 mg/kg i.p., in 10 mL/kg Mean Total Bone Volume +/- SEM for Each Study Group Group A    Bortezomib  0.6 mg/kg, i.p., in 10 mL/kg
Group B    MOR202      1 mg/kg, i.v., in 10 mL/kg
Group C    Vehicle Control (0.9% Saline for Injection) i.p., 10 mL/kg
Group AB   Bortezomib/MOR202    0.6/1 mg/kg, i.p./i.v., in 10 mL/kg

SEQUENCE LISTING

```
<160> NUMBER OF SEQ ID NOS: 22

<210> SEQ ID NO 1
<211> LENGTH: 10
<212> TYPE: PRT
<213> ORGANISM: artificial sequence
<220> FEATURE:
<221> NAME/KEY: SOURCE
<222> LOCATION: 1..10
<223> OTHER INFORMATION: /mol_type="protein"
      /note="HCDR1"
      /organism="synthetic construct"

<400> SEQUENCE: 1

Gly Phe Thr Phe Ser Ser Tyr Tyr Met Asn
1               5                   10

<210> SEQ ID NO 2
```

```
<211> LENGTH: 17
<212> TYPE: PRT
<213> ORGANISM: artificial sequence
<220> FEATURE:
<221> NAME/KEY: SOURCE
<222> LOCATION: 1..17
<223> OTHER INFORMATION: /mol_type="protein"
      /note="HCDR2"
      /organism="synthetic construct"

<400> SEQUENCE: 2

Gly Ile Ser Gly Asp Pro Ser Asn Thr Tyr Tyr Ala Asp Ser Val Lys
1               5                   10                  15
Gly

<210> SEQ ID NO 3
<211> LENGTH: 11
<212> TYPE: PRT
<213> ORGANISM: artificial sequence
<220> FEATURE:
<221> NAME/KEY: SOURCE
<222> LOCATION: 1..11
<223> OTHER INFORMATION: /mol_type="protein"
      /note="HCDR3"
      /organism="synthetic construct"

<400> SEQUENCE: 3

Asp Leu Pro Leu Val Tyr Thr Gly Phe Ala Tyr
1               5                   10

<210> SEQ ID NO 4
<211> LENGTH: 11
<212> TYPE: PRT
<213> ORGANISM: artificial sequence
<220> FEATURE:
<221> NAME/KEY: SOURCE
<222> LOCATION: 1..11
<223> OTHER INFORMATION: /mol_type="protein"
      /note="LCDR1"
      /organism="synthetic construct"

<400> SEQUENCE: 4

Ser Gly Asp Asn Leu Arg His Tyr Tyr Val Tyr
1               5                   10

<210> SEQ ID NO 5
<211> LENGTH: 7
<212> TYPE: PRT
<213> ORGANISM: artificial sequence
<220> FEATURE:
<221> NAME/KEY: SOURCE
<222> LOCATION: 1..7
<223> OTHER INFORMATION: /mol_type="protein"
      /note="LCDR2"
      /organism="synthetic construct"

<400> SEQUENCE: 5

Gly Asp Ser Lys Arg Pro Ser
1               5

<210> SEQ ID NO 6
<211> LENGTH: 9
<212> TYPE: PRT
<213> ORGANISM: artificial sequence
<220> FEATURE:
<221> NAME/KEY: SOURCE
<222> LOCATION: 1..9
<223> OTHER INFORMATION: /mol_type="protein"
      /note="LCDR3"
      /organism="synthetic construct"
```

-continued

```
<400> SEQUENCE: 6

Gln Thr Tyr Thr Gly Gly Ala Ser Leu
1               5

<210> SEQ ID NO 7
<211> LENGTH: 300
<212> TYPE: PRT
<213> ORGANISM: Homo sapiens
<220> FEATURE:
<221> NAME/KEY: SOURCE
<222> LOCATION: 1..300
<223> OTHER INFORMATION: /mol_type="protein"
      /note="CD38"
      /organism="Homo sapiens"

<400> SEQUENCE: 7

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 8
```

<211> LENGTH: 128
<212> TYPE: PRT
<213> ORGANISM: artificial sequence
<220> FEATURE:
<221> NAME/KEY: SOURCE
<222> LOCATION: 1..128
<223> OTHER INFORMATION: /mol_type="protein"
    /note="variable heavy chain"
    /organism="synthetic construct"

<400> SEQUENCE: 8

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Ser Trp Ile Arg Gln Ser Pro Gly Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Leu Asp His Arg Tyr His Glu Asp Thr Val Tyr
            100                 105                 110

Pro Gly Met Asp Val Trp Gly Gln Gly Thr Leu Val Thr Val Ser Ser
        115                 120                 125
```

<210> SEQ ID NO 9
<211> LENGTH: 109
<212> TYPE: PRT
<213> ORGANISM: artificial sequence
<220> FEATURE:
<221> NAME/KEY: SOURCE
<222> LOCATION: 1..109
<223> OTHER INFORMATION: /mol_type="protein"
    /note="variable light chain"
    /organism="synthetic construct"

<400> SEQUENCE: 9

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Pro Ala Tyr Thr Val
            20                  25                  30

Thr Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Trp Asp Pro Ser Ser Gly Val
                85                  90                  95

Val Phe Gly Gly Gly Thr Lys Leu Thr Val Leu Gly Gln
            100                 105
```

<210> SEQ ID NO 10
<211> LENGTH: 120
<212> TYPE: PRT
<213> ORGANISM: artificial sequence
<220> FEATURE:
<221> NAME/KEY: SOURCE
<222> LOCATION: 1..120

<223> OTHER INFORMATION: /mol_type="protein"
     /note="variable heavy chain"
     /organism="synthetic construct"

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
            115                 120

<210> SEQ ID NO 11
<211> LENGTH: 109
<212> TYPE: PRT
<213> ORGANISM: artificial sequence
<220> FEATURE:
<221> NAME/KEY: SOURCE
<222> LOCATION: 1..109
<223> OTHER INFORMATION: /mol_type="protein"
     /note="variable light chain"
     /organism="synthetic construct"

<400> SEQUENCE: 11

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
            85                  90                  95

Val Phe Gly Gly Gly Thr Lys Leu Thr Val Leu Gly Gln
            100                 105

<210> SEQ ID NO 12
<211> LENGTH: 360
<212> TYPE: DNA
<213> ORGANISM: artificial sequence
<220> FEATURE:
<221> NAME/KEY: source
<222> LOCATION: 1..360
<223> OTHER INFORMATION: /mol_type="DNA"
     /note="variable heavy domain"
     /organism="synthetic construct"

<400> SEQUENCE: 12

```
caggtgcaat tggtggaaag cggcggcggc ctggtgcaac cgggcggcag cctgcgtctg    60
agctgcgcgg cctccggatt tacctttttct tcttattata tgaattgggt gcgccaagcc   120
cctgggaagg gtctcgagtg ggtgagcggt atctctggtg atcctagcaa tacctattat   180
gcggatagcg tgaaaggccg ttttaccatt tcacgtgata attcgaaaaa cacccctgtat  240 ctgcaaatga acagcctgcg tgcggaagat acggccgtgt attattgcgc gcgtgatctt   300
cctcttgttt atactggttt tgcttattgg ggccaaggca ccctggtgac ggttagctca   360
```

```
<210> SEQ ID NO 13
<211> LENGTH: 327
<212> TYPE: DNA
<213> ORGANISM: artificial sequence
<220> FEATURE:
<221> NAME/KEY: source
<222> LOCATION: 1..327
<223> OTHER INFORMATION: /mol_type="DNA"
     /note="variable light chain"
     /organism="synthetic construct"

<400> SEQUENCE: 13
```

```
gatatcgaac tgacccagcc gccttcagtg agcgttgcac caggtcagac cgcgcgtatc    60
tcgtgtagcg gcgataatct tcgtcattat tatgtttatt ggtaccagca gaaacccggg   120
caggcgccag ttcttgtgat ttatggtgat tctaagcgtc cctcaggcat cccggaacgc   180
tttagcggat ccaacagcgg caacaccgcg accctgacca ttagcggcac tcaggcggaa   240
gacgaagcgg attattattg ccagacttat actggtggtg cttctcttgt gtttggcggc   300
ggcacgaagt taaccgttct tggccag                                       327
```

```
<210> SEQ ID NO 14
<211> LENGTH: 5
<212> TYPE: PRT
<213> ORGANISM: artificial sequence
<220> FEATURE:
<221> NAME/KEY: SOURCE
<222> LOCATION: 1..5
<223> OTHER INFORMATION: /mol_type="protein"
     /note="HCDR1"
     /organism="synthetic construct"

<400> SEQUENCE: 14

Ser Tyr Tyr Met Asn
1               5

<210> SEQ ID NO 15
<211> LENGTH: 5
<212> TYPE: PRT
<213> ORGANISM: artificial sequence
<220> FEATURE:
<221> NAME/KEY: SOURCE
<222> LOCATION: 1..5
<223> OTHER INFORMATION: /mol_type="protein"
     /note="HCDR1"
     /organism="synthetic construct"

<400> SEQUENCE: 15

Asp Tyr Trp Met Gln
1               5

<210> SEQ ID NO 16
<211> LENGTH: 17
<212> TYPE: PRT
<213> ORGANISM: artificial sequence
<220> FEATURE:
<221> NAME/KEY: SOURCE
```

```
<222> LOCATION: 1..17
<223> OTHER INFORMATION: /mol_type="protein"
      /note="HCDR2"
      /organism="synthetic construct"

<400> SEQUENCE: 16

Thr Ile Tyr Pro Gly Asp Gly Asp Thr Gly Tyr Ala Gln Lys Phe Gln
1               5                   10                  15
Gly

<210> SEQ ID NO 17
<211> LENGTH: 11
<212> TYPE: PRT
<213> ORGANISM: artificial sequence
<220> FEATURE:
<221> NAME/KEY: SOURCE
<222> LOCATION: 1..11
<223> OTHER INFORMATION: /mol_type="protein"
      /note="HCDR3"
      /organism="synthetic construct"

<400> SEQUENCE: 17

Gly Asp Tyr Tyr Gly Ser Asn Ser Leu Asp Tyr
1               5                   10

<210> SEQ ID NO 18
<211> LENGTH: 11
<212> TYPE: PRT
<213> ORGANISM: artificial sequence
<220> FEATURE:
<221> NAME/KEY: SOURCE
<222> LOCATION: 1..11
<223> OTHER INFORMATION: /mol_type="protein"
      /note="LCDR1"
      /organism="synthetic construct"

<400> SEQUENCE: 18

Lys Ala Ser Gln Asp Val Ser Thr Val Val Ala
1               5                   10

<210> SEQ ID NO 19
<211> LENGTH: 7
<212> TYPE: PRT
<213> ORGANISM: artificial sequence
<220> FEATURE:
<221> NAME/KEY: SOURCE
<222> LOCATION: 1..7
<223> OTHER INFORMATION: /mol_type="protein"
      /note="LCDR2"
      /organism="synthetic construct"

<400> SEQUENCE: 19

Ser Ala Ser Tyr Arg Tyr Ile
1               5

<210> SEQ ID NO 20
<211> LENGTH: 9
<212> TYPE: PRT
<213> ORGANISM: artificial sequence
<220> FEATURE:
<221> NAME/KEY: SOURCE
<222> LOCATION: 1..9
<223> OTHER INFORMATION: /mol_type="protein"
      /note="LCDR3"
      /organism="synthetic construct"

<400> SEQUENCE: 20

Gln Gln His Tyr Ser Pro Pro Tyr Thr
1               5
```

```
<210> SEQ ID NO 21
<211> LENGTH: 120
<212> TYPE: PRT
<213> ORGANISM: artificial sequence
<220> FEATURE:
<221> NAME/KEY: SOURCE
<222> LOCATION: 1..120
<223> OTHER INFORMATION: /mol_type="protein"
      /note="varaible heavy chain"
      /organism="synthetic construct"

<400> SEQUENCE: 21

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
        50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 22
<211> LENGTH: 109
<212> TYPE: PRT
<213> ORGANISM: artificial sequence
<220> FEATURE:
<221> NAME/KEY: SOURCE
<222> LOCATION: 1..109
<223> OTHER INFORMATION: /mol_type="protein"
      /note="variable light chain"
      /organism="synthetic construct"

<400> SEQUENCE: 22

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
                20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
        50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg Thr
            100                 105
```

ANTI-CD38 ANTIBODY AND LENALIDOMIDE OR BORTEZOMIB FOR THE TREATMENT OF MULTIPE MYELOMA AND NHL

CROSS REFERENCE TO RELATED APPLICATIONS

This application claims the benefit of U.S. provisional application Ser. No. 61/486,814 filed May 17, 2011, U.S. provisional application Ser. No. 61/468,607 filed Mar. 29, 2011, U.S. provisional application Ser. No. 61/437,696 filed Jan. 31, 2011, and U.S. provisional application Ser. No. 61/386,619 filed Sep. 27, 2010, which are all incorporated by reference in their entireties.

BACKGROUND

Multiple myeloma is a B cell malignancy characterized by the latent accumulation in bone marrow of secretory plasma cells with a low proliferative index and an extended life span. The disease ultimately attacks bones and bone marrow, resulting in multiple tumors and lesions throughout the skeletal system.

Approximately 1% of all cancers, and slightly more than 10% of all hematologic malignancies, can be attributed to multiple myeloma (MM). The incidence of MM increases in the aging population, with the median age at time of diagnosis being about 61 years. The currently available therapies for multiple myeloma include chemotherapy, stem cell transplantation, Thalomid® (thalidomide), Velcade® (bortezomib), Aredia® (pamidronate), and Zometa® (zoledronic acid). The current treatment protocols, which include a combination of chemotherapeutic agents such as vincristine, BCNU, melphalan, cyclophosphamide, adriamycin, and prednisone or dexamethasone, yield a complete remission rate of only about 5%, and median survival is approximately 36-48 months from the time of diagnosis. Recent advances using high dose chemotherapy followed by autologous bone marrow or peripheral blood mononuclear cell transplantation have increased the complete remission rate and remission duration. Yet overall survival has only been slightly prolonged, and no evidence for a cure has been obtained. Ultimately, MM patients often relapse, even under maintenance therapy with interferon-alpha (IFN-α) alone or in combination with steroids.

Non-Hodgkin's lymphoma is a broad classification of lymphomas, which are cancers originating from the lymphatic system when lymphocytes (B-cells or T-cells) become malignant and proliferate uncontrollably to form a tumor mass. In total NHL encompasses around 30 different subtypes of lymphoma, including Diffuse large B-cell lymphoma (DLBCL) and follicular lymphoma (FL). The incidence of NHL will reach over 140,000 in the major markets by 2019. The available treatment options include Rituxan/MabThera, combinations thereof, such as, R-CHOP (rituximab, cyclophosphamide, doxorubicin, vincristine and prednisone), R-CVP (Rituxan, cyclophosphamide, vincristine and prednisone), and chemotherapy. In addition, following remission or after relapse, hematopoietic stem cell transplantation may be considered. Despite the current treatment options, however, the survival rates within high risk groups of aggressive NHL can be as low as 30% over 5 years. Therefore, there remains a high unmet need for effective treatments and combination treatments.

CD38 is an example of an antigen expressed on such malignant plasma cells, and other lymphocytes. Functions ascribed to CD38 include both receptor mediation in adhesion and signaling events and (ecto-) enzymatic activity. As an ectoenzyme, CD38 uses NAD+ as substrate for the formation of cyclic ADP-ribose (cADPR) and ADPR, but also of nicotinamide and nicotinic acid-adenine dinucleotide phosphate (NAADP). cADPR and NAADP have been shown to act as second messengers for Ca2+ mobilization. By converting NAD+ to cADPR, CD38 regulates the extracellular NAD+ concentration and hence cell survival by modulation of NAD-induced cell death (NCID). In addition to signaling via Ca2+, CD38 signaling occurs via cross-talk with antigen-receptor complexes on T and B cells or other types of receptor complexes, e.g. MHC molecules, and is in this way involved in several cellular responses, but also in switching and secretion of IgG.

Antibodies specific for CD38 are described in WO1999/62526 (Mayo Foundation); WO200206347 (Crucell Holland); US2002164788 (Jonathan Ellis) which is incorporated by reference in its entirety; WO2005/103083 (MorphoSys AG), U.S. Ser. No. 10/588,568, which is incorporated by reference in its entirety, WO2006/125640 (MorphoSys AG), U.S. Ser. No. 11/920,830, which is incorporated by reference in its entirety, and WO2007/042309 (MorphoSys AG), U.S. Ser. No. 12/089,806, which is incorporated by reference in its entirety; WO2006099875 (Genmab), U.S. Ser. No. 11/886,932, which is incorporated by reference in its entirety; and WO08/047,242 (Sanofi-Aventis), U.S. Ser. No. 12/441,466, which is incorporated by reference in its entirety.

Combinations of antibodies specific for CD38 and other agents are described in WO200040265 (Research Development Foundation); WO2006099875 and WO2008037257 (Genmab); and WO2010061360, WO2010061359, WO2010061358 and WO2010061357 (Sanofi Aventis), which are all incorporated by reference in their entireties.

It is clear that in spite of the recent progress in the discovery and development of anti-cancer agents, many forms of cancer involving CD38-expressing tumors still have a poor prognosis. Thus, there is a need for improved methods for treating such forms of cancer.

SUMMARY

In one aspect, the present disclosure relates to a synergistic combination of an antibody specific for CD38 and thalidomide or an analog thereof, e.g. lenalidomide. In another aspect the present disclosure relates to a synergistic combination comprising an antibody specific for CD38 and bortezomib or other proteasome inhibitor. Such combinations are useful in the treatment of cancers, such as, multiple myeloma and/or non-Hodgkin's lymphoma.

In vitro and in vivo models are considered predictive of how a certain compound or combination of compounds would behave in humans. Here, the combinations of an antibody specific for CD38 and lenalidomide was tested in human multiple myeloma cell lines and synergy was identified. In addition the combination of an antibody specific for CD38 and lenalidomide, and a combination of an antibody specific for CD38 and bortezomib were tested in mouse models against both multiple myeloma cells and Burkitt's lymphoma (a form of NHL) cells and synergy was identified. Therefore, the combinations will be effective in the treatment of humans in multiple myeloma and/or non-Hodgkin's lymphoma. In addition, the antibody specific to CD38 exemplified in the present specification is entering into clinical trials, where such combinations can be confirmed in humans.

When compounds are combined either in vitro or in vivo, one expects that the combination has only additive effects.

Quite unexpectedly, the inventors found that the combination of a particular anti-CD38 antibody and lenalidomide mediated a synergistic level of Antibody-Dependent Cell-Mediated Cytotoxicity (ADCC) in both the AMO-1 and NCI-H929 multiple myeloma cell lines. In addition, and also unexpectedly, a particular anti-CD38 antibody when combined with lenalidomide or when combined with bortezomib mediated a synergistic level of reduction in bone lysis in the NCI-H929 SCID mouse model and synergistically increased the median survival days in the RAMOS SCID mouse model. Therefore, both the combination of the exemplified antibody specific for CD38 and lenalidomide and the exemplified antibody specific for CD38 and bortezomib behaved synergistically in the in vitro and/or in vivo models relevant to multiple myeloma and/or non-Hodgkin's lymphoma.

An aspect of the present disclosure comprises a combination wherein the antibody specific for CD38 comprises an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and the thalidomide or an analog thereof is lenalidomide. In preferred aspects, the combination is used for the treatment of multiple myeloma and/or non-Hodgkin's lymphoma.

An aspect of the present disclosure comprises a combination wherein the antibody specific for CD38 comprises an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and the proteasome inhibitor is bortezomib. In preferred aspects, the combination is used for the treatment of multiple myeloma and/or non-Hodgkin's lymphoma.

DESCRIPTION OF DRAWINGS

FIG. 10 shows the mediation of ADCC on LP-1 cells by the combination of MOR202 at 15 μg/ml and Velcade® (bortezomib). The two charts represent two different donors.

FIG. 11 shows the amino acid sequence of MOR202.

FIGS. 13-18 show the Chou factor synergy analysis for six separate experiments using the combination of MOR202 and lenalidomide in the mediation of ADCC on AMO-1 cells. FIG. 13 shows experiment 1. FIG. 14 shows experiment 2. FIG. 15 shows experiment 3. FIG. 16 shows experiment 4. FIG. 17 shows experiment 5. FIG. 18 shows experiment 6. FIGS. 13-15 were derived from the three experiments shown in Tables 3a-c, and FIG. 3. FIGS. 16-18 were derived from the three experiments shown in Tables 4a-c, and FIG. 4.

DETAILED DESCRIPTION OF THE INVENTION

Figure 1:
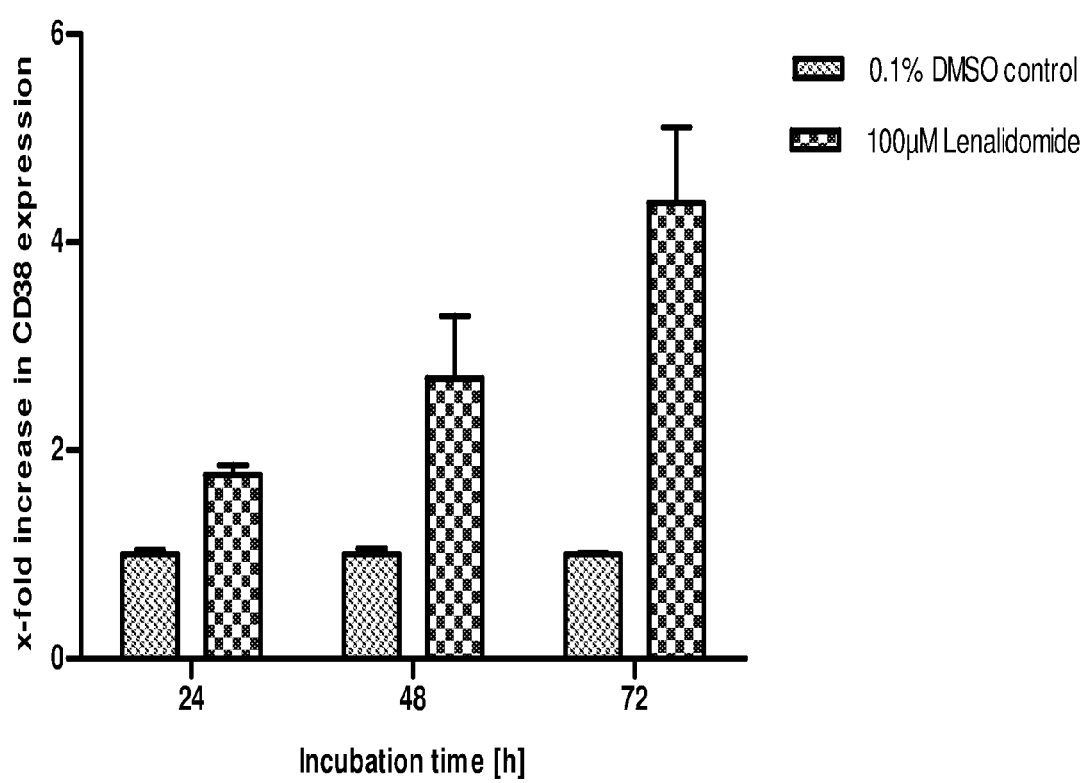
FIG. 1 shows the effects of lenalidomide alone on the expression of CD38 in AMO-1 cells.

"Synergy", "synergism" or "synergistic" mean more than the expected additive effect of a combination. The "synergy", "synergism" or "synergistic" effect of a combination is determined herein by the methods of Chou et al., and/or Clarke et al. See Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety. In Chou et al., multiple methods of determining synergism are disclosed and at least one of these methods is used herein. See also Clarke et al., Issues in experimental design and endpoint analysis in the study of experimental cytotoxic agents in vivo in breast cancer and other models, Breast Cancer Research and Treatment 46:255-278 (1997), which is incorporated by reference in its entirety.

The term "antibody" means monoclonal antibodies, including any isotype, such as, IgG, IgM, IgA, IgD and IgE. An IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab' F(ab')2 fragment, or other fragment, which contains at least one variable heavy or variable light chain, each containing CDRs and framework regions.

THALOMID® (thalidomide) in combination with dexamethasone is indicated for the treatment of patients with newly diagnosed multiple myeloma, and is marketed by Celgene.

A "thalidomide analog" includes, but is not limited to, thalidomide itself, lenalidomide (CC-5013, Revlimid™), Pomalidomide (CC4047, Actimid™) and the compounds disclosed in WO2002068414 and WO2005016326, which are incorporated by reference in their entireties. The term refers to a synthetic chemical compound using the thalidomide structure as a backbone (e.g., side groups have been added or such groups have been deleted from the parent structure). The analog differs in structure from thalidomide and its metabolite compounds such as by a difference in the length of an alkyl chain, a molecular fragment, by one or more functional groups, or a change in ionization. The term "thalidomide analog" also includes the metabolites of thalidomide. Thalidomide analogs include the racemic mixture of the S— and the R-enantiomer of a respective compound and the S-enantiomer or to the R-enantiomer individually. The racemic mixture is preferred. Thalidomide analogs include the compounds of the following structures:

(A) Lenalidomide

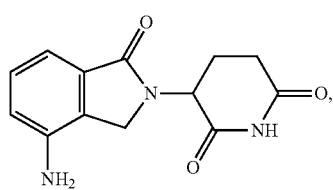

(Formula 1)

(B) Thalidomide

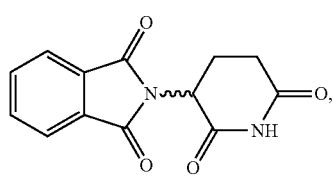

(Formula 2)

(C) Pomalidomide

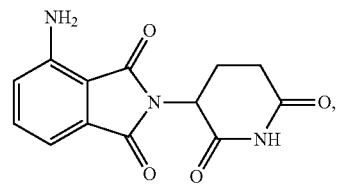

(Formula 3)

(D)

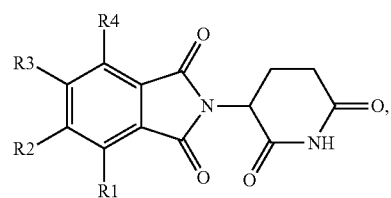

(Formula 4)

wherein R21, R22, R23, and R24 are each independently H, alkoxy, amino, or alkylamine, and (E)

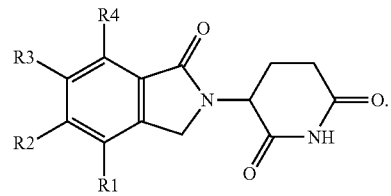

(Formula 5)

wherein R21, R22, R23, and R24 are each independently H, alkoxy, amino, or alkylamine. Lenalidomide is currently marketed as Revlimid® by Celgene for the treatment of multiple myeloma. Lenalidomide is described as having at least the following properties in relation to the treatment of tumors, a) cytotoxic to tumor cells, Gandhi et al., Lenalidomide inhibits proliferation of Namalwa CSN.70 cells and interferes with Gab1 phosphorylation and adaptor protein complex assembly, Leuk Res., 30(7):849-58 (2006), which is incorporated by reference in its entirety; b) activates natural killer (Nk) cells, Gandhi et al., Dexamethasone synergizes with lenalidomide to inhibit multiple myeloma tumor growth, but reduces lenalidomide-induced immunomodulation of T and NK cell function, Curr Cancer Drug Targets, 1; 10(2):155-67 (March 2010), which is incorporated by reference in its entirety; and c) upregulates CD38 expression on tumor cells, See Lapalombella et al., Lenalidomide down-regulates the CD20 antigen and antagonizes direct and antibody-dependent cellular cytotoxicity of rituximab on primary chronic lymphocytic leukemia cells, Blood, 112:13, 5180-5189 (15 Dec. 2008), which is incorporated by reference in its entirety. "LEN" is used to describe lenalidomide.

As described, thalidomide analogs upregulate the expression of CD38 on tumor cells. Other agents that upregulate the expression of CD38 on the surface of tumor cells are described in WO00/40265, U.S. Ser. No. 09/226,895, which is incorporated by reference in its entirety (Research Development Foundation).

A "proteasome inhibitor" refers to a compound that blocks the action of proteasomes, i.e. cellular complexes that break down proteins, such as for example the p53 protein. Several classes of proteasome inhibitors are known. The class of the peptide boronates includes bortezomib (INN, PS-341; Velcade®), a compounds which is approved in the U.S. for the treatment of relapsed multiple myeloma. Another peptide boronate is CEP-18770. Other classes of proteasome inhibitors include peptide aldehydes (e.g. MG132), peptide vinyl sulfones, peptide epoxyketones (e.g. epoxomicin, carfilzomib), β lactone inhibitors (e.g. lactacystin, MLN 519, NPI-0052, Salinosporamide A), compounds which create dithiocarbamate complexes with metals (e.g. Disulfuram, a drug which is also used for the treatment of chronic alcoholism), and certain antioxidants (e.g. Epigallocatechin-3-gallate) catechin-3-gallate, and Salinosporamide A.

"VH" refers to the variable region of an immunoglobulin heavy chain of an antibody, or antibody fragment. "VL" refers to the variable region of the immunoglobulin light chain of an antibody, or antibody fragment.

The term "CD38" refers to the protein known as CD38, having the following synonyms: ADP-ribosyl cyclase 1, cADPr hydrolase 1, Cyclic ADP-ribose hydrolase 1, T10.

Human CD38 has the amino acid sequence of:

```
                                        (SEQ ID NO: 7)
MANCEFSPVSGDKPCCRLSRRAQLCLGVSILVLILVVVLAVVVPRWRQQW

SGPGTTKRFPETVLARCVKYTEIHPEMRHVDCQSVWDAFKGAFISKHPCN

ITEEDYQPLMKLGTQTVPCNKILLWSRIKDLAHQFTQVQRDMFTLEDTLL

GYLADDLTWCGEFNTSKINYQSCPDWRKDCSNNPVSVFWKTVSRRFAEAA

CDVVHVMLNGSRSKIFDKNSTFGSVEVHNLQPEKVQTLEAWVIHGGREDS

RDLCQDPTIKELESIISKRNIQFSCKNIYRPDKFLQCVKNPEDSSCTSEI.
```

"MOR202" an anti-CD38 antibody whose amino acid sequence is provided in FIG. 11. "MOR202" and "MOR03087" are used as synonyms to describe the antibody shown in FIG. 11.

The DNA sequence encoding the MOR202 Variable Heavy Domain is:

```
                                       (SEQ ID NO: 12)
CAGGTGCAATTGGTGGAAAGCGGCGGCGGCCTGGTGCAACCGGGCGGCAG

CCTGCGTCTGAGCTGCGCGGCCTCCGGATTTACCTTTTCTTCTTATTATA

TGAATTGGGTGCGCCAAGCCCCTGGGAAGGGTCTCGAGTGGGTGAGCGGT

ATCTCTGGTGATCCTAGCAATACCTATTATGCGGATAGCGTGAAAGGCCG

TTTTACCATTTCACGTGATAATTCGAAAAACACCCTGTATCTGCAAATGA

ACAGCCTGCGTGCGGAAGATACGGCCGTGTATTATTGCGCGCGTGATCTT

CCTCTTGTTTATACTGGTTTTGCTTATTGGGGCCAAGGCACCCTGGTGAC

GGTTAGCTCA
```

The DNA sequence encoding the MOR202 Variable Light Domain is:

```
                                       (SEQ ID NO: 13)
GATATCGAACTGACCCAGCCGCCTTCAGTGAGCGTTGCACCAGGTCAGAC

CGCGCGTATCTCGTGTAGCGGCGATAATCTTCGTCATTATTATGTTTATT

GGTACCAGCAGAAACCCGGGCAGGCGCCAGTTCTTGTGATTTATGGTGAT

TCTAAGCGTCCCTCAGGCATCCCGGAACGCTTTAGCGGATCCAACAGCGG

CAACACCGCGACCCTGACCATTAGCGGCACTCAGGCGGAAGACGAAGCGG

ATTATTATTGCCAGACTTATACTGGTGGTGCTTCTCTTGTGTTTGGCGGC

GGCACGAAGTTAACCGTTCTTGGCCAG
```

Antibody "Ref mAB5" is an anti-CD38 antibody whose amino acid sequence is provided below (the CDRs are bolded and underlined):

```
VH:
                                       (SEQ ID NO: 21)
QVQLVQSGAEVAKPGTSVKLSCKASGYTFTDYWMQWVKQRPGQGLEWIGT

IYPGDGDTGYAQKFQGKATLTADKSSKTVYMHLSSLASEDSAVYYCARGD

YYGSNSLDYWGQGTSVTVSS

VL:
                                       (SEQ ID NO: 22)
DIVMTQSHLSMSTSLGDPVSITCKASQDVSTVVAWYQQKPGQSPRRLIYS

ASYRYIGVPDRFTGSGAGTDFTFTISSVQAEDLAVYYCQQHYSPPYTFGG

GTKLEIKRT
```

The CDRs of Ref mAB5 are defined by Kabat et al. and an antibody having the same CDRs as Ref mAB5 is described in WO2008/047242, U.S. Ser. No. 12/441,466, which is incorporated by reference in its entirety.

"Fc region" means the constant region of an antibody, which in humans may be of the IgG1, 2, 3, 4 subclass or others. The sequences of human Fc regions are available at IMGT, Human IGH C-REGIONs.

"Enhances ADCC activity" means an increase in the mediation of antibody dependent cell-mediated cytotoxicity. Amino acid modifications within the Fc region that result in an enhancement of ADCC activity are disclosed in WO200042072 Genentech, WO2004029207A2 Xencor, and WO2004063351A2 Macrogenics, which are all incorporated by reference in their entireties.

"MOR03207" is an antibody whose amino acid sequence is:

```
VH:
                                       (SEQ ID NO: 8)
QVQLQQSGPGLVKPSQTLSLTCAISGDSVSSNSAAWSWIRQSPGRGLEWL

GRIYYRSKWYNDYAVSVKSRITINPDTSKNQFSLQLNSVTPEDTAVYYCA

RLDHRYHEDTVYPGMDVWGQGTLVTVSS

VL:
                                       (SEQ ID NO: 9)
DIELTQPPSVSVAPGQTARISCSGDNLPAYTVTWYQQKPGQAPVLVIYDD

SDRPSGIPERFSGSNSGNTATLTISGTQAEDEADYYCASWDPSSGVVFGG

GTKLTVLGQ.
```

MOR03207 binds lysozyme, and is used as isotype control, as it is IgG1.

A "combination" means more than one item, e.g. a compound such as an antibody and lenalidomide.

The present disclosure also relates to combinations, pharmaceuticals, and pharmaceutical compositions containing the described combinations. The two components of the synergistic combination of the present invention, e.g. the antibody specific for CD38 and lenalidomide, may be administered together, or separately. When administered together, the two components may be formulated together in one pharmaceutical composition, which may include a pharmaceutical acceptable carrier or excipient. Alternatively the two components might also be formulated in different pharmaceutical compositions. In this case the two components can be administered simultaneously or subsequently. In an embodiment, the thalidomide or an analog thereof, e.g. lenalidomide, is administered prior to and/or separately from the administration of the antibody specific for CD38, e.g. MOR202. In a further embodiment, lenalidomide, is administered at least 72 hours prior to administration of the antibody specific for CD38, e.g. MOR202. This time period allows for lenalidomide mediated upregulation of CD38 in the target cells.

A pharmaceutical composition includes an active agent, eg. an antibody for therapeutic use in humans. A pharmaceutical composition may include acceptable carriers or excipients.

"Administered" or "administration" includes but is not limited to delivery by an injectable form, such as, for example, an intravenous, intramuscular, intradermal or subcutaneous route or mucosal route, for example, as a nasal spray or aerosol for inhalation or as an ingestable solution, capsule or tablet.

A "therapeutically effective amount" of a compound or combination refers to an amount sufficient to cure, alleviate or partially arrest the clinical manifestations of a given disease or disorder and its complications. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

Surprisingly, it was found that the combination of a particular anti-CD38 antibody and lenalidomide mediated a synergistic level of Antibody-Dependent Cell-Mediated Cytotoxicity (ADCC) in both AMO-1 and NCI-H929 multiple myeloma cells. In addition, and also unexpectedly, a particular anti-CD38 antibody when combined with lenalidomide mediated a synergistic level of reduction in bone lysis in the NCI-H929 SCID mouse model and synergistically increased the median survival days in the RAMOS SCID mouse model. Therefore, the combination of the exemplified antibody specific for CD38 and lenalidomide behaved synergistically in both the in vitro and in vivo models relevant to multiple myeloma and/or non-Hodgkin's lymphoma. Therefore, this combination yields synergistic results in the treatment of multiple myeloma and/or non-Hodgkin's lymphoma in humans.

Lenalidomide is a thalidomide analog, therefore, it is expected that other thalidomide analogs, such as, pomalidomide or thalidomide itself also lead to synergistic effects when used in combination with an anti-CD38 antibody. In addition, as thalidomide or an analog thereof upregulate CD38 expression in multiple myeloma cell lines, therefore, it is expected that synergism should result when other agents that upregulate the expression of CD38 on the surface of tumor cells, e.g. trans-retinoic acid, and anti-CD38 antibodies are used in combination.

Surprisingly, it was found that the combination of a particular anti-CD38 antibody and bortezomib mediated a high level of Antibody-Dependent Cell-Mediated Cytotoxicity (ADCC) in the NCI-H929 and LP-1 multiple myeloma cell lines. In addition, and also surprisingly it was found that the combination of a particular anti-CD38 antibody and bortezomib mediated a synergistic level of reduction in bone lysis in the NCI-H929 SCID mouse model and synergistically increased the median survival days in the RAMOS SCID mouse model. Therefore, the combination of the exemplified antibody specific for CD38 and bortezomib behaved synergistically in the in vivo models relevant to multiple myeloma and/or non-Hodgkin's lymphoma. Therefore, this combination yields synergistic results in the treatment of multiple myeloma and/or non-Hodgkin's lymphoma in humans.

It is expected that other proteasome inhibitors, such as, Disulfuram, Epigallocatechin-3-gallate, and Salinosporamide A will lead to similar effects when used in combination with an anti-CD38 antibody.

The "CDRs" herein are defined by either Chothia et al., Kabat et al. or by an internal numbering convention. See Chothia C, Lesk A M. (1987) Canonical structures for the hypervariable regions of immunoglobulins. J Mol. Biol., 196 (4):901-17, which is incorporated by reference in its entirety. See Kabat E. A, Wu T. T., Perry H. M., Gottesman K. S. and Foeller C. (1991). Sequences of Proteins of Immunological Interest. 5th edit., NIH Publication no. 91-3242, US Dept. of Health and Human Services, Washington, D.C., which is incorporated by reference in its entirety.

Embodiments

An aspect of the present disclosure comprises a synergistic combination of an antibody specific for CD38 and (a) thalidomide or an analog thereof, or (b) a proteasome inhibitor, for use in the treatment of multiple myeloma and/or non-hodgkins lymphoma.

An aspect of the present disclosure comprises a combination of an antibody specific for CD38 and thalidomide or an analog thereof. In embodiments, the combination is synergistic.

In embodiments, the antibody specific for CD38 comprises an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGASL (SEQ ID NO: 6).

In embodiments, the antibody specific for CD38 comprises an HCDR1 region of sequence DYWMQ (SEQ ID NO: 15), an HCDR2 region of sequence TIYPGDGDTGYAQKFQG (SEQ ID NO: 16), an HCDR3 region of sequence GDYYGSNSLDY (SEQ ID NO: 17), an LCDR1 region of sequence KASQDVSTVVA (SEQ ID NO: 18), an LCDR2 region of sequence SASYRYI (SEQ ID NO: 19), and an LCDR3 region of sequence QQHYSPPYT (SEQ ID NO: 20).

In an aspect the combination is used for the treatment of multiple myeloma and/or non-hodgkins lymphoma. Embodiments comprise a combination, wherein the thalidomide analog is lenalidomide.

An aspect relates to pharmaceutical compositions comprising the combinations. In embodiments, the composition comprises an acceptable carrier. In embodiments, the composition is administered in an effective amount.

An aspect of the present disclosure comprises a synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and lenalidomide for the treatment of multiple myeloma and/or non-hodgkins lymphoma.

A further embodiment comprises a combination, wherein the antibody comprises a variable heavy chain of the sequence QVQLVESGGGLVQPGGSLRLSCAASGFTFSSYYMNWVRQAPGKGLEWVSGISGDPSNTYYADSVKGRFTISRDNSKNTLYLQMNSLRAEDTAVYYCARDLPLVYTGFAYWGQGTLVTV SS (SEQ ID NO: 10) and a variable light chain of the sequence DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVLGQ (SEQ ID NO: 11).

An aspect of the present disclosure comprises a synergistic combination of an antibody specific for CD38 comprising an HCDR1 region of sequence DYWMQ (SEQ ID NO: 15), an HCDR2 region of sequence TIYPGDGDTGYAQKFQG (SEQ ID NO: 16), an HCDR3 region of sequence GDYYGSNSLDY (SEQ ID NO: 17), an LCDR1 region of sequence KASQDVSTVVA (SEQ ID NO: 18), an LCDR2 region of sequence SASYRYI (SEQ ID NO: 19), and an LCDR3 region of sequence QQHYSPPYT (SEQ ID NO: 20) and lenalidomide for the treatment of multiple myeloma and/or non-hodgkins lymphoma.

A further embodiment comprises a combination, wherein the antibody comprises a variable heavy chain of the sequence QVQLVQSGAEVAKPGTSVKLSCKASGYTFTDYWMQWVKQRPGQGLEWIGTIYPGDGDTGYAQKFQGKATLTADKSSKTVYMHLSSLASEDSAVYYCARGDYYGSNSLDYWGQGTSV TVSS (SEQ ID NO: 21) and a variable light chain of the sequence DIVMTQSHLSMSTSLGDPVSITCKASQDVSTVVAWYQQKPGQSPRRLIYSASYRYIGVPDRFTGSGAGTDFTFTISSVQAEDLAVYYCQQHYSPPYTFGGGTKLEIKRT (SEQ ID NO: 22).

In embodiments the antibody has an IgG1 Fc region. In embodiments the antibody comprises a modified Fc region, wherein said modification enhances ADCC activity.

In another aspect, the components of the combination, the antibody specific for CD38 and lenalidomide, are administered separately. In an embodiment, lenalidomide is administered prior to administration of the antibody specific for CD38. In a further embodiment, lenalidomide is administered at least 72 hours prior to administration of the antibody specific for CD38.

In another aspect the synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and lenalidomide is able to mediate killing of CD38-expressing AMO-1 cells and/or NCI-H929 cells by ADCC in the presence of isolated human PBMCs with an at least two-fold, three-fold, four-fold, or five-fold better efficacy than lenalidomide alone.

In another aspect the synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and lenalidomide is able to reduce bone lysis with an at least two-fold, three-fold, four-fold, or five-fold better efficacy than lenalidomide alone.

Another aspect comprises a method of treating multiple myeloma and/or non-hodgkins lymphoma in an individual in need thereof, which method comprises administration of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and lenalidomide to an individual having multiple myeloma or non-hodgkins lymphoma. In embodiments, the combination is administered in an effective amount.

Another aspect comprises a combination comprising an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and lenalidomide. In an embodiment, the combination is used for the treatment of cancer. In a further embodiment, the cancer is selected from multiple myeloma, and non-hodgkins lymphoma.

Another aspect comprises a combination of an antibody specific for CD38 and a proteasome inhibitor. In embodiments, the combination is synergistic. In embodiments, the antibody specific for CD38 comprises an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6).

In an aspect the combination is used for the treatment of multiple myeloma and/or non-hodgkins lymphoma. In embodiments, the combination comprises a proteasome inhibitor, which is bortezomib. An aspect relates to pharmaceutical compositions comprising the combinations. In embodiments, the composition comprises an acceptable carrier. In embodiments, the composition is administered in an effective amount.

An aspect of the present disclosure comprises a synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and bortezomib for the treatment of multiple myeloma and/or non-hodgkins lymphoma.

A further embodiment comprises a combination, wherein the antibody comprises a variable heavy chain of the sequence QVQLVESGGGLVQPGGSLRLSCAASG-FTFSSYYMNWVRQAPGKGLEWVSGISGDPSNT YYADSVKGRFTISRDNSKNTLYLQMNSL-RAEDTAVYYCARDLPLVYTGFAYWGQGTLVTV SS (SEQ ID NO: 10) and a variable light chain of the sequence DIELTQPPSVSVAPGQTARISCSGDNL-RHYYVYWYQQKPGQAPVLVIYGDSKRPSGIPER FSGSNSGNTATLTISGTQAEDEADYYCQ-TYTGGASLVFGGGTKLTVLGQ (SEQ ID NO: 11).

In embodiments the antibody has an IgG1 Fc region. In embodiments the antibody comprises a modified Fc region, wherein said modification enhances ADCC activity.

In an embodiment, the combination is used for the treatment of cancer. In a further embodiment, the cancer is selected from multiple myeloma, and non-hodgkins lymphoma.

In another aspect, the components of the combination, the antibody and proteasome inhibitor, are administered separately.

In another aspect the synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and bortezomib is able to mediate killing of CD38-expressing LP-1 cells and/or NCI-H929 cells by ADCC in the presence of isolated human PBMCs with an at least two-fold, three-fold, four-fold, or five-fold better efficacy than bortezomib alone.

In another aspect the synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and bortezomib is able to reduce bone lysis with an at least two-fold, three-fold, four-fold, or five-fold better efficacy than bortezomib alone.

In another aspect, the present disclosure comprises a method of treating multiple myeloma and/or non-hodgkins lymphoma in an individual in need thereof, which method comprises administration of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and bortezomib to an individual having multiple myeloma or non-hodgkins lymphoma.

In embodiments, the combination is administered in an effective amount.

Another aspect comprises a combination comprising an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and bortezomib.

An aspect comprises a synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and
(a) thalidomide or an analog thereof, or
(b) a proteasome inhibitor,
for use in the treatment of multiple myeloma and/or non-hodgkins lymphoma.

Embodiments comprise a combination, wherein the antibody comprises a variable heavy chain of the sequence QVQLVESGGGLVQPGGSLRLSCAASG-FTFSSYYMNWVRQAPGKGLEWVSGISGDPSNT YYADSVKGRFTISRDNSKNTLYLQMNSL-RAEDTAVYYCARDLPLVYTGFAYWGQGTLVTV SS (SEQ ID NO: 10) and a variable light chain of the sequence DIELTQPPSVSVAPGQTARISCSGDNL-RHYYVYWYQQKPGQAPVLVIYGDSKRPSGIPER FSGSNSGNTATLTISGTQAEDEADYYCQ-TYTGGASLVFGGGTKLTVLGQ (SEQ ID NO: 11).

Embodiments comprise a combination, wherein the antibody comprises an IgG1 Fc region. Embodiments comprise a combination, wherein the antibody comprises a modified Fc region, wherein said modification enhances ADCC activity.

Embodiments comprise a combination, wherein said antibody specific for CD38 and said thalidomide or an analog thereof or proteasome inhibitor are administered separately.

Embodiments comprise a combination, which is able to reduce bone lysis with an at least two-fold better efficacy than lenalidomide and/or bortezomib alone.

Embodiments comprise a combination, wherein said antibody specific for CD38 is combined with thalidomide or an analog thereof. Embodiments comprise a combination, wherein the thalidomide analog comprises lenalidomide. Embodiments comprise a combination, wherein lenalidomide is administered prior to administration of the antibody specific for CD38. Embodiments comprise a combination, wherein lenalidomide is administered at least 72 hours prior to administration of the antibody specific for CD38.

Embodiments comprise a combination of an antibody specific for CD38 and lenalidomide, which is able to mediate killing of CD38-expressing AMO-1 and/or NCI-H929 cells by ADCC in the presence of isolated human PBMCs with an at least two-fold better efficacy than lenalidomide alone.

Embodiments comprise a combination, comprising said antibody specific for CD38 and a proteasome inhibitor. In some embodiments, the proteasome inhibitor is bortezomib. Embodiments comprise a combination of an antibody specific for CD38 and bortezomib, which is able to mediate killing of CD38-expressing LP-1 and/or NCI-H929 cells by ADCC in the presence of isolated human PBMCs with an at least two-fold better efficacy than bortezomib alone.

An aspect comprises a synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and lenalidomide or other thalidomide analog for use in the treatment of multiple myeloma and/or non-hodgkins lymphoma.

An aspect comprises a synergistic combination of an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and bortezomib or other proteasome inhibitor for use in the treatment of multiple myeloma and/or non-hodgkins lymphoma.

EXAMPLES

Example 1

CD38 Expression on the Surface of Various Cell Lines

The cell lines of Table 1 were tested for levels of CD38 expression.

TABLE 1

| Cell Line | Supplied by: | Cultivated in: |
|---|---|---|
| AMO-1: Multiple Myeloma Cell Line | DSMZ #ACC 538 | RPMI1640, with L-Glutamine, (PAN Biotech GmbH, Cat No.: P04-16500 medium) |
| LP1: Multiple Myeloma Cell Line | DSMZ #ACC 41 | Iscove's Modified Dulbecco's Medium (IMDM) with GlutaMAX ™ (Invitrogen, Cat No.: 31980-048) |
| NCI-H929: Multiple Myeloma Cell Line | DSMZ #ACC 163 | RPMI1640 (same as AMO-1), supplemented with 1 mM Na-Pyruvate, 50 µM β-Mercaptoethanol |
| RPMI8226: Multiple Myeloma Cell Line | DSMZ #ACC 402 | RPMI1640 (same as AMO-1) |
| OPM-2: Multiple Myeloma Cell Line | DSMZ #ACC 50 | RPMI1640 (same as AMO-1) |
| Plasmacytoma, Malignant Plasma Cells | Klinikum rechts der Isar | RPMI1640 (same as AMO-1) |

Bone marrow samples (4-10 ml aspirate) from multiple myeloma patients and extramedullary tumor plasmacytoma samples were obtained after informed consent from the Klinikum rechts der Isar ("KrdI") (Munich, Germany). Samples were subjected to centrifugation, and further plasma cell enrichment was achieved via magnetic-activated cell sorting.

Cells were stained with a directly labelled QuantiBRITE™ CD38-PE antibody (Becton Dickinson GmbH, Clone HB7, CAT #342371), which is specific for CD38. The "Antibodies Bound Per Cell" (ABC's) were determined using the flow cytometry based QuantiBRITE™ system, which measures the geometric mean (GeoMean) per cell. Conversion of measured GeoMean into correlating ABC amount per cell was done with GraphPad PRISM™ software. The ABC values are assumed to correlate with the number of CD38 molecules per cell, since QuantiBRITE™ CD38-PE carries one PE molecule per antibody. The results are shown in Table 2.

Example 2

Evaluation of Effect of Lenalidomide on Upregulation of CD38 in Various Cell Lines To determine whether lenalidomide induced upregulation of CD38 in the multiple myeloma and plasmacytoma cells of Table 1, the cell lines were incubated with 100 µM lenalidomide and, subsequently, CD38 surface expression was analyzed by FACS.

Materials and Methods

Around $2 \times 10^5$ cells of each of the cells lines of Table 1 were plated on 48-well dishes in standard RPMI medium. Lenalidomide, purchased from Selleck Chemicals (LLC S1029, CAS No. 191732-6; Batch: S10290), was applied to respective wells to a final concentration of 100 µM in a volume of 750 µl containing 20% FCS and 0.1% DMSO. As negative control 0.1% DMSO in FCS-supplemented medium was used and plates were incubated for 24 h, 48 h and 72 h at 37° C. and 5% $CO_2$ in humidified incubator.

Cells were resuspended by gentle pipetting and 250 µl of cell suspension per incubation period were transferred into a well of a 96-well round bottom plate. Cells were washed by centrifugation for 1 min at 700×g and were resuspended in 150 µl of cold FACS buffer (1×PBS supplemented with 3% FCS). Cells were again pelleted down by centrifugation and were resuspended in 150 µl of FACS buffer containing 15 µg/ml of anti-CD38 antibody (MOR202, IgG1) or control antibody MOR03207 and incubated for 1 h on ice. Cells were then washed 3 times by centrifugation and were resuspended in FACS buffer supplemented with PE-labeled secondary antibody (PE-Fab$_2$ fragment, goat anti-human IgG, Fc-fragment specific; Jackson Immuno Research; CAT: 109-116-098; Lot: 80938). Cells were incubated for 45 minutes on ice, then washed 3 times by centrifugation and resuspended in FACS buffer. The cell suspensions were then subjected to FACS analysis using a FACS array device.

Figure 5:
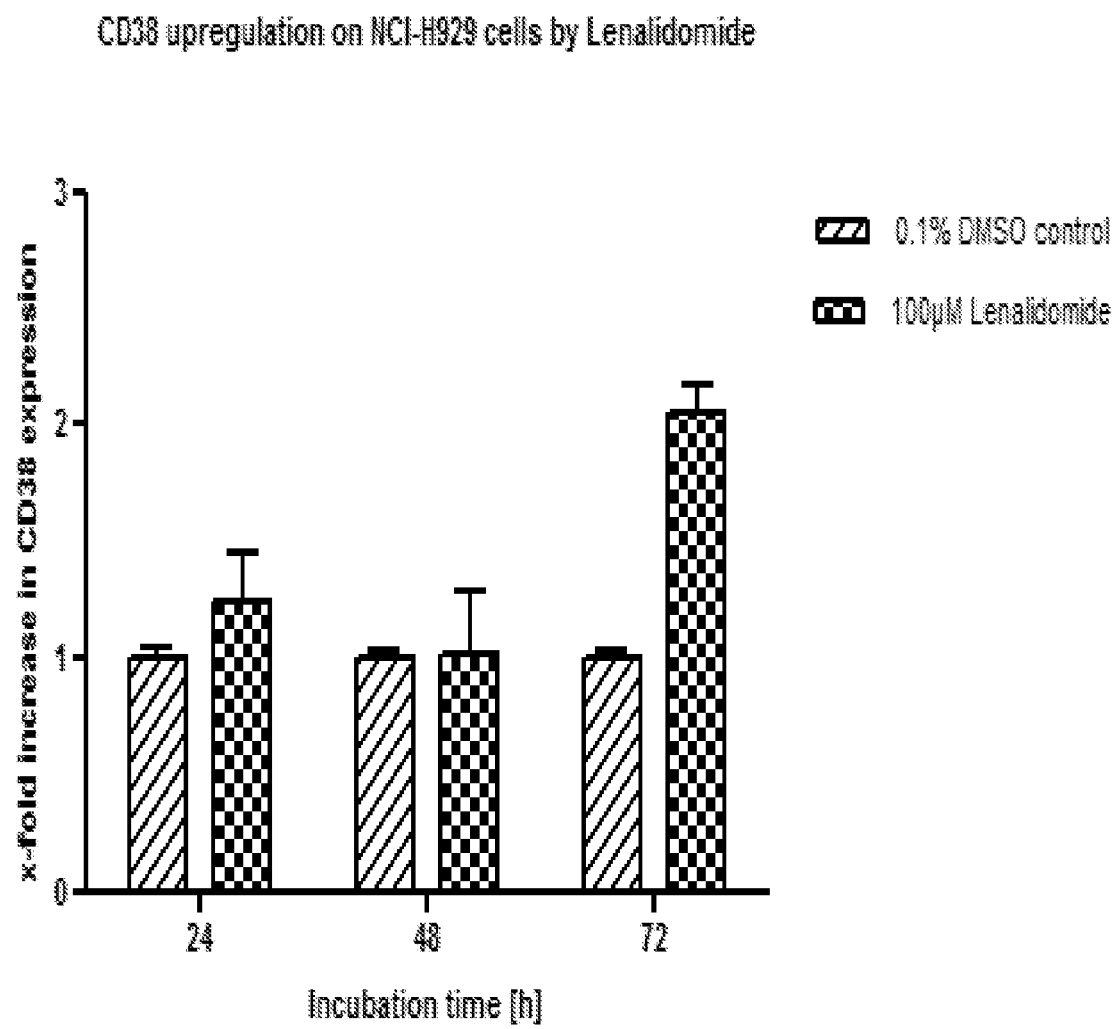
FIG. 5 shows the effects of lenalidomide alone on the expression of CD38 in NCI-H929 cells.

The basal CD38 expression of each cell line and the affect of lenalidomide on CD38 expression are shown in Table 2. Additionally, the affect of lenalidomide on the CD38 expression of AMO-1 cells is shown in FIG. 1, and the affect of lenalidomide on the CD38 expression of NCI-H929 cells is shown in FIG. 5.

TABLE 2

| | Absolute number of ABC (CD38 expression) | | | | |
|---|---|---|---|---|---|
| Cell line | Basal | LEN (extrapolated) | IN-CREASE | Fold increase | Effect |
| AMO-1 | 25,000 | 115,000 | 90,000 | 4.6 | Significant |
| LP-1 | 125,000 | 162,500 | 37,500 | 1.3 | No |
| NCI-H929 | 195,000 | 390,000 | 195,000 | 2.0 | Weak |
| RPMI-8226 | 670,000 | 871,000 | 199,000 | 1.3 | Weak |
| OPM-2 | 38,000 | 98,800 | 60,800 | 2.6 | Significant |
| Plasmacytoma | 30,000 | 69,000 | 39,000 | 2.3 | Significant |

Example 3

Inhibition of Proliferation of AMO-1 Cells Using Lenalidomide Alone

The cytotoxicity of Lenalidomide was tested in AMO-1 cells. Cells were collected and distributed in 96-well plates with 5000 cells per well. Increasing amounts of Lenalidomide were added to the wells and plates were incubated for 24 h, 48 h and 72 h at 37° C. in a humidified incubator (5% $CO_2$).

Figure 2:
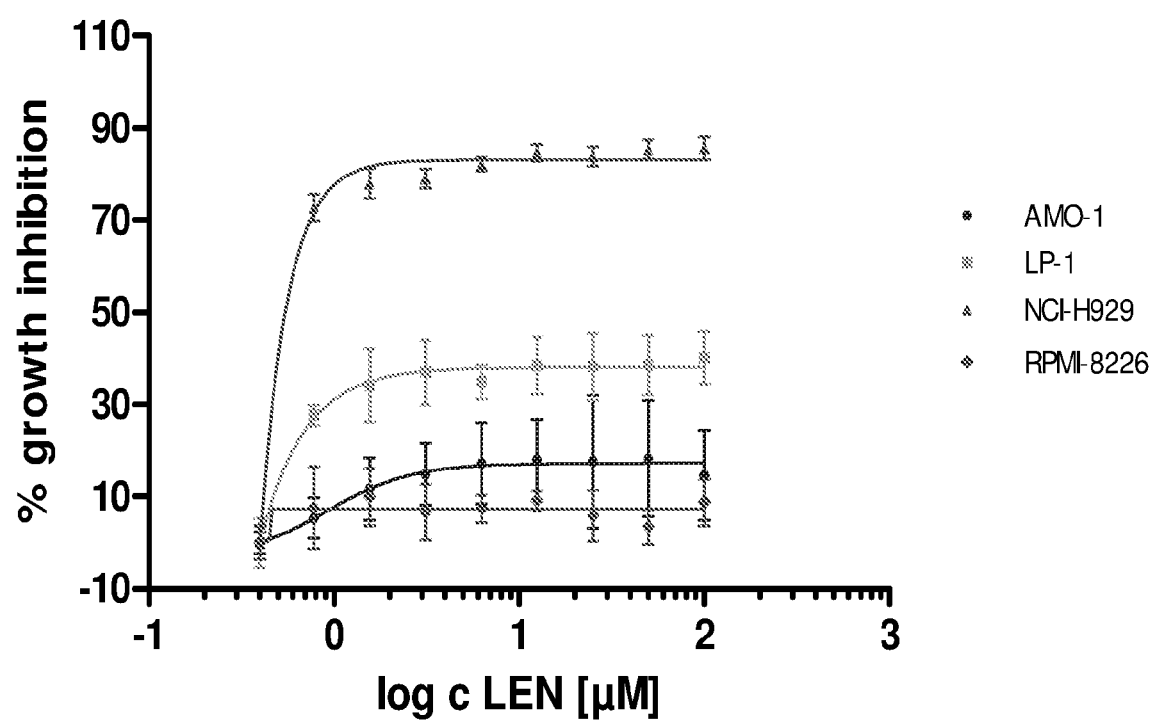
FIG. 2 shows the effects of lenalidomide alone on cell proliferation in various multiple myeloma cell lines. This measure represents the relative cytotoxicity of lenalidomide on each cell line.

After incubation, plates were analyzed for cell proliferation in a quantitative colorimietric XTT-based assay using the cell proliferation kit II (ROCHE, Cell Proliferation Kit II, Cat. No.: 11465015001). For subsequent measurement plates were subjected to Tecan Genios Reader and absorbance at 492 nm was detected. The results are shown in FIG. 2.

Example 4

Synergistic Combination of MOR0202 and Lenalidomide in AMO-1 Cells

AMO-1 cells were selected for testing with the combination of MOR202 and lenalidomide. AMO-1 cells are similar to plasmacytoma cells in humans in that both have a low basal CD38 expression, and CD38 is significantly upregulated in both upon treatment with lenalidomide as shown in Table 2.

PBMC's were isolated by density gradient centrifugation of freshly isolated human blood. Isolated blood from different donors were layered on a defined volume of Biocoll (Biochrome AG; CAT No.:L6115; LOT No.:1050T) in a Falcon tube and centrifuged at 380 g. The PBMCs were isolated and supplemented with RPMI medium.

After 72 h, cells were counted and the PBMCs were adjusted to a concentration of $6.6 \times 10^6$/ml while the AMO-1 cells were adjusted to a final concentration of $2.5 \times 10^5$/ml. For later identification in flow cytometry, the AMO-1 cells were stained for 3 min with 0.1 µg/ml of CalceinAM (Calcein: 1 mg/ml stock solution, Invitrogen, Cat No.: C3099) and washed three times by gentle centrifugation. 100 µl of target cell suspension were mixed with 100 µl of PBMCs to achieve a ratio of 1:30. Antibody MOR202 or antibody MOR03207 (negative control) were added to a final concentration of 15 µg/ml. Cell suspensions were further incubated for 4 h at 37° C. To detect dead AMO-1 cells, cell suspensions were challenged with propidium iodide (PI) and subsequently analyzed in flow cytometry. Target cells were separated via gating of CalceinAM positive cell populations, and cells killed via ADCC were quantified.

In total six experiments were performed in order to determine the mediation of ADCC on AMO-1 cells by the combination of MOR202 and lenalidomide. In three experiments, the PBMCs and AMO-1 cells were treated with lenalidomide prior to treatment with MOR202, the results are shown in Tables 3 a-c and FIG. 3. In three additional experiments, only the PBMCs were treated with lenalidomide prior to treatment with MOR202, the results are shown in Tables 4 a-c and FIG. 4.

Table 3 Both Effector and AMO-1 cells were treated with Lenalidomide prior to treatment with MOR202. Single and combination doses of 10 µM LEN and 15 µg/ml of MOR03207 and MOR202 were used.

The data is presented in the following three ways, as a) raw data (% dead cells), b) normalized specific killing data, where the MOR202 treatment group is set as 1 (100%), and c) normalized specific killing data, where the theoretical combination is set as 1 (100%). Table 3a represents raw data.

TABLE 3a

| AMO-1 | LEN 10 µM alone | MOR202 alone (15 µg/ml) | Combination of LEN (10 µM) and MOR202 (15 µg/ml) | DMSO | MOR03207 (15 µg/ml) | MOR03207 (15 µg/ml) + DMSO | LEN (0 µM) | LEN (10 µM) alone without PBMCs | DMSO control without PBMCs |
|---|---|---|---|---|---|---|---|---|---|
| Exp. 1 | 12.89 | 23.69 | 35.98 | 13.10 | 14.15 | 15.12 | 15.45 | 15.41 | 11.07 |
| Exp. 2 | 10.13 | 22.53 | 29.09 | 7.94 | 10.52 | 6.99 | 13.22 | 8.44 | 8.45 |
| Exp. 3 | 22.80 | 49.56 | 80.39 | 19.93 | 24.04 | 22.24 | 22.63 | 22.38 | 26.43 |

The units of the values listed are % dead cells. The DMSO, MOR03207, MOR03207+DMSO, LEN0, LEN10 without PBMCs and DMSO without PBMCs groups are controls.

Table 3b represents the data of Table 3a, but normalized, where the MOR202 treatment group is set as 1 (100%).

TABLE 3b

| AMO-1 | MOR03207 (15 µg/ml) | MOR202 (15 µg/ml) | LEN alone (10 µM) | Theoretical combination | MOR202 (15 µg/ml) and LEN (10 µM) |
|---|---|---|---|---|---|
| Exp. 1 | −0.1 | 1.0 | 0.0 | 1.0 | 2.2 |
| Exp. 2 | −0.2 | 1.0 | 0.2 | 1.2 | 1.8 |
| Exp. 3 | 0.1 | 1.0 | 0.1 | 1.1 | 2.3 |

Figure 3:
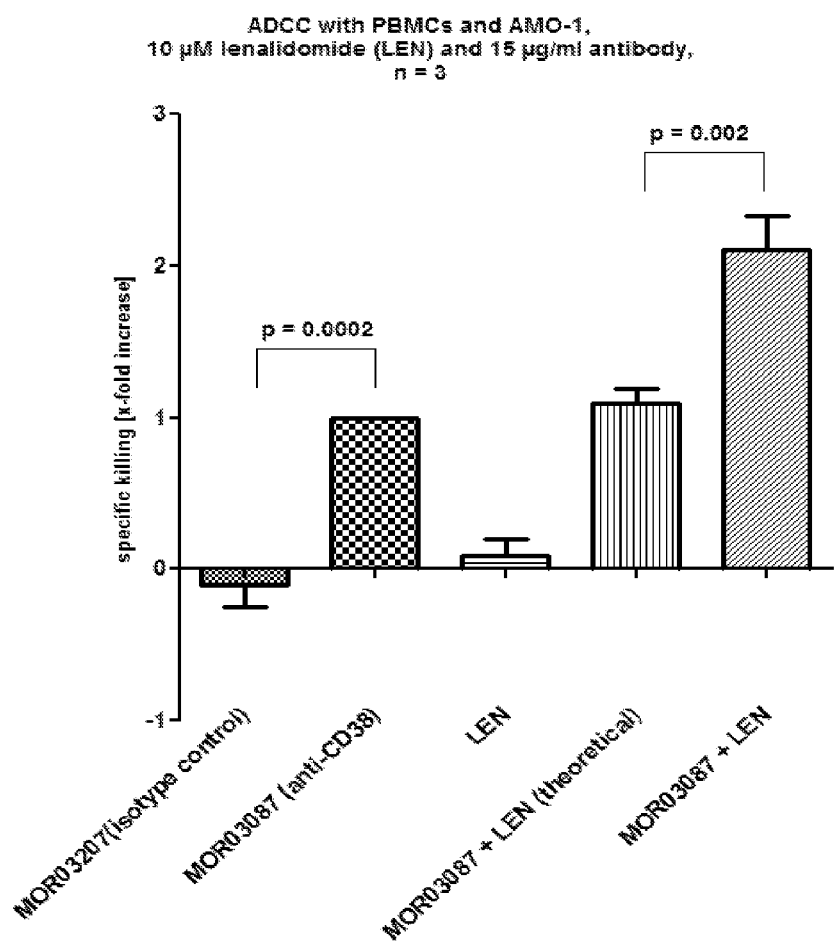
FIG. 3 shows the mediation of ADCC on AMO-1 cells by the combination of MOR03087 and lenalidomide. The PBMCs and AMO-1 cells were treated with lenalidomide prior to treatment with MOR03087. MOR03207 binds lysosyme, and is used as isotype control, as it is IgG1. LEN represents lenalidomide. "Theoretical" represents the addition of the value of MOR03087 alone and the value of LEN alone. The data shown are the averages from Table 3b.

For Tables 3b-c, "Theoretical Combination" represents the addition of the values of MOR202 alone and the values of LEN alone. The normalized data of Table 3b is calculated as follows. Table 3a represents the number of dead cells. Therefore, the specific killing values of Table 3b are calculated by subtracting the values of the controls. Then the specific killing values are compared to the MOR202 group, which is set as 1. The averages of the results in Table 3b are shown in FIG. 3.

1. Determination of Synergism 1.1 Chou et al.

The methods of Chou-Talalay were used to determine synergism. See Chou T C, Talalay P, Quantitative analysis of dose-effect relationships: the combined effects of multiple drugs or enzyme inhibitors. Adv Enzyme Regul 22: 27-55 (1984), which is incorporated by reference in its entirety. Synergism analysis is carried out using the Cl-isobol method.

Median-Effect Equation

The median-effect equation models of the effect of an inhibitor (such as a drug) as $$F_a/F_u = (D/D50)^m$$

where D is the dose, $F_a$ and $F_u$ is the fraction of the system affected and unaffected by the dose D ($F_a+F_u=1$); D50 is the dose producing the median effect (e.g. IC50, ED50, LD50). The constant m determines the shape of the dose-effect curve. We used Excel Fit software to carry out a linear regression calculation to estimate the parameters m and D50.

The effects of the combination on AMO-1 cells is measured % cell death as described above. We define the fraction F, to be the ratio of % cell death of the treated cell line to the % cell death of the cell line exposed to a control. That is:

$F_u$=% cell death(treated cell line)/% cell death(non-treated cell line)

Then the % cell death of a cell line is the constant D50 in the median effect equation, which can be estimated by the linear regression described above.

CI-Isobol Method

The CI-isobol method provides a quantitative assessment of synergism between drugs. A combination index (CI) is estimated from dose-effect data of single and combined drug treatments. A value of CI less than 1 indicates synergism; CI=1 indicates additive effect; and CI>1 indicates antagonism. Synergistic ranges are further defined by Chou and Talahay for CI values<0.1 as very strong synergism, CI values between 0.1 and 0.3 as strong synergism, CI values of 0.3-0.7 as synergism, CI values of 0.7-0.9 as moderate to slight synergism. Drug interaction (synergism or antagonism) is more pronounced the farther a CI value is from 1.

Formally, the combination index (CI) of a combined drug treatment is defined as $CI = D_1/D_{x1} + D_2/D_{x2}$ Here D1 and D2 are the doses of drug 1 and drug 2, respectively, in the combination; Dx1, and Dx2 each is the dose of a treatment with only drug 1 and drug 2 that would give the same effect as that of the combination, respectively. The doses Dx1 and Dx2 need to be estimated from the dose-effect data of single drug treatments. Essentially, a median effect equation is fitted to the data of each drug. From the median effect equation of a drug, we can estimate the dose (i.e. D) necessary to produce an effect (i.e. Fa, Fu). The further a point lies from the additive line, the bigger the different between 1 and its CI, thus the stronger the (synergistic or antagonistic) effect is.

The above method is described in Chou T C, Talalay P, Quantitative analysis of dose-effect relationships: the combined effects of multiple drugs or enzyme inhibitors. Adv Enzyme Regul 22: 27-55 (1984), which is incorporated by reference in its entirety. An additional review of the above Chou method is also provided in Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety.

Figure 12:
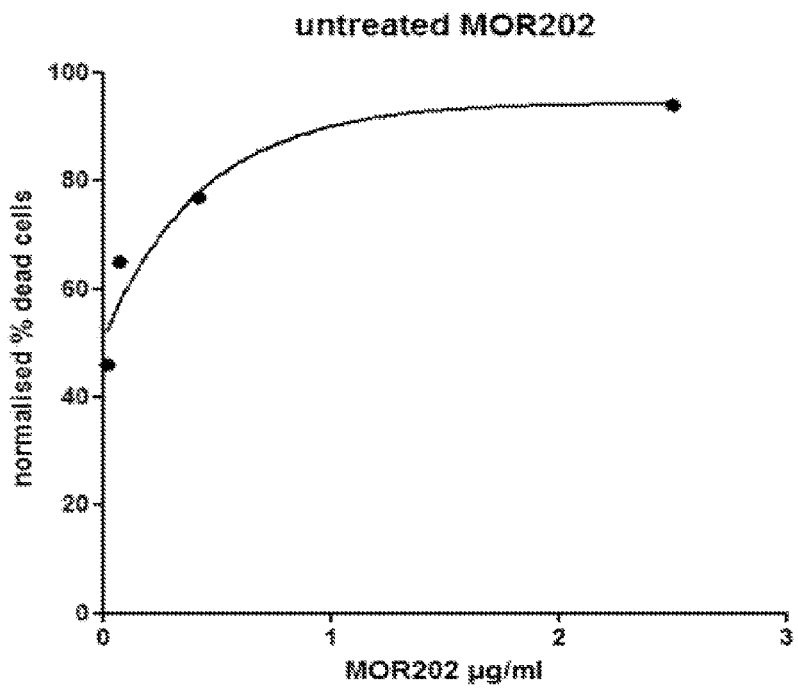
FIG. 12 shows the Best Fit curve, as described in Chou et al., of the MOR202 and lenalidomide combination in the mediation of ADCC on AMO-1 cells and it is also representative for the Best Fit curve generated for analysis of the mediation of ADCC on NCI-H929 cells.

The curves generated for the Chou based synergy calculations are shown in FIGS. 12-18. In FIG. 12, the best fit curve was determined by removing the data points a) where the concentration of MOR202 was too low to have any effect and b) where the concentration was near saturation. At the appropriate date point, approx. 80% cell killing, the CI value is less than 1, supporting clear synergy. FIGS. 13-18 represent the six experiments from Tables 3 and 4, and in each the Dx1 (dose of MOR202) needed to reach 100% effect of the combination of MOR 202 and lenalidomide goes to infinity; therefore, the $D_1/D_{x1}$ is less than 1 and as lenalidomide has no effect on AMO-1 cells regarding cell killing, the Dx2 value also approaches infinity, so the $D_2/D_{x2}$ approximates 0, therefore the CI values of each of the six experiments is less than 1, supporting clear synergy.

Table 3c represents the normalization of data, where the theoretical combination is set as 1 (100%) and includes the CI Chou calculations.

TABLE 3c

| Cell line | Experiment | MOR202 (0.42 µg/ml) | LEN (5 µM) | Theoretical Combination | MOR202 (0.42 µg/ml) and LEN (5 µM) | Combination Index (CI) | Conclusion |
|---|---|---|---|---|---|---|---|
| AMO-1 | Experiment 1 | 0.6 | 0.4 | 1.0 | 1.0 | <<0.1 * | synergy |
| | Experiment 2 | 0.9 | 0.1 | 1.0 | 2.4 | <<0.1 * | synergy |
| | Experiment 3 | 0.9 | 0.1 | 1.0 | 1.8 | <<0.1 * | synergy |
| | AVERAGE | 0.8 | 0.2 | 1.0 | 1.7 | — | — |

The date shown in Table 3c differs from Tables 3a and 3b. Table 3c is based upon different raw data points than shown in Table 3a, as the concentrations chosen in Table 3c are closer to the $EC_{50}$ of the antibody (raw data not shown). "Theoretical Combination" represents the addition of the values of MOR202 alone and the values of LEN alone.

Table 4 Effector cells only treated with Lenalidomide prior to treatment with MOR202. Single and combination doses of 10 µM LEN and 15 µg/ml of MOR03207 and MOR202 were used.

The data is presented in the following three ways, as a) raw data (% dead cells), b) normalized specific killing data, where the MOR202 treatment group is set as 1 (100%), and c) normalized specific killing data, where the theoretical combination is set as 1 (100%). Table 4a represents raw data.

TABLE 4a

| AMO-1 | LEN 10 µM alone | MOR202 alone (15 µg/ml) | Combination of LEN (10 µM) and MOR202 (15 µg/ml) | DMSO | MOR03207 15 µg/ml | MOR03207 15 µg/ml + DMSO | LEN (0 µM) |
|---|---|---|---|---|---|---|---|
| Exp. 1 | 15.33 | 23.09 | 23.46 | 14.62 | 16.17 | 15.97 | 12.87 |
| Exp. 2 | 12.98 | 21.08 | 25.75 | 10.24 | 12.17 | 11.45 | 9.78 |
| Exp. 3 | 17.93 | 48.28 | 56.49 | 16.75 | 17.42 | 15.77 | 18.16 |

The units of the values listed are % dead cells. The DMSO, MOR03207, MOR03207+DMSO, LEN0, LEN10 without PBMCs and DMSO without PBMCs are controls.

TABLE 4b

| AMO-1  | MOR03207 (15 µg/ml) | MOR202 (15 µg/ml) | LEN alone (10 µM) | Theoretical combination | MOR202 (15 µg/ml) and LEN (10 µM) |
|--------|---------------------|-------------------|-------------------|-------------------------|-----------------------------------|
| Exp. 1 | 0.5                 | 1.0               | 0.1               | 1.1                     | 1.1                               |
| Exp. 2 | 0.3                 | 1.0               | 0.3               | 1.3                     | 1.6                               |
| Exp. 3 | 0.0                 | 1.0               | 0.0               | 1.0                     | 1.3                               |

Table 4b represents the data of Table 4a, but normalized, where the MOR202 treatment group is set as 1 (100%). For Tables 4b-c, "Theoretical combination" represents the values of MOR202 alone plus the values of LEN alone.

Figure 4:
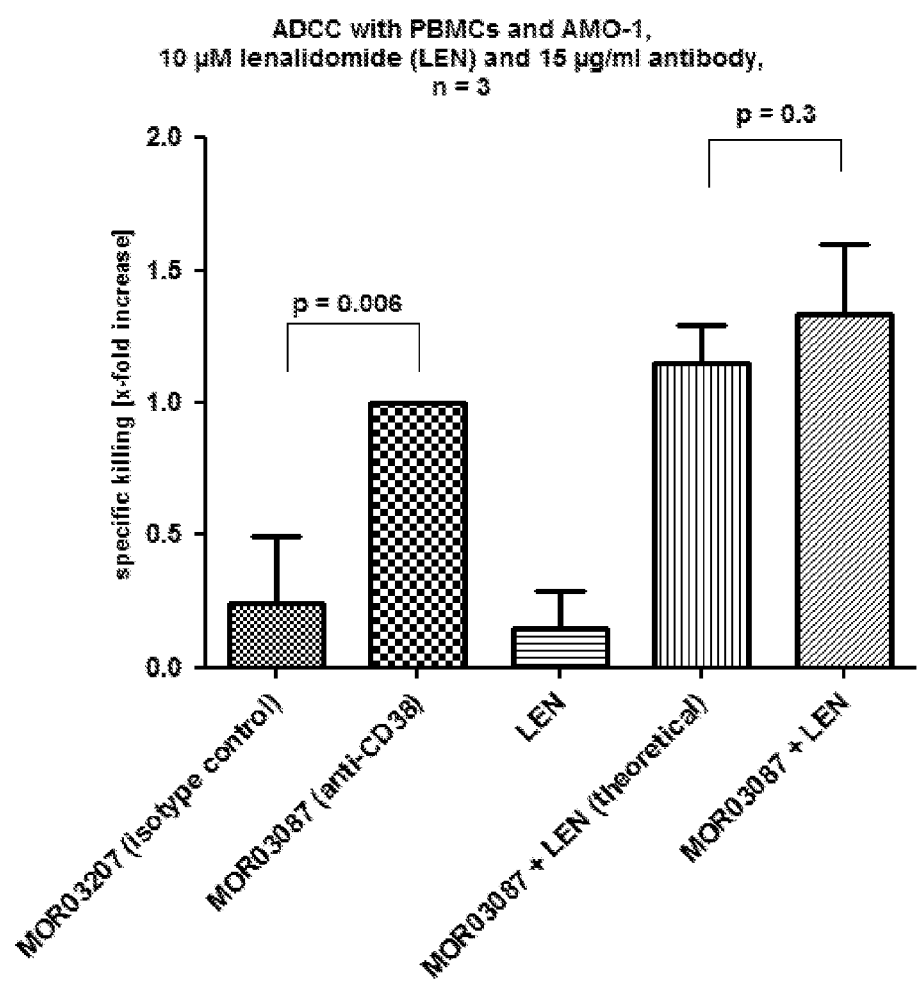
FIG. 4 shows the mediation of ADCC on AMO-1 cells by the combination of MOR03087 and lenalidomide. Only the PBMCs were treated with lenalidomide prior to treatment with MOR03087. MOR03207 binds lysosyme, and is used as isotype control, as it is IgG1. LEN represents lenalidomide. "Theoretical" represents the addition of the value of MOR03087 alone and the value of LEN alone. The data shown are the averages from Table 4b.

The normalization of the data as shown in Table 4b is calculated as described in Table 3b, by substracting the controls. The averages of the results of Table 4b are shown in FIG. 4.

TABLE 4c

| Cell line | Experiment   | MOR202 (0.42 µg/ml) | LEN (5 µM) | Theoretical Combination | MOR202 (0.42 µg/ml) and LEN (5 µM) | Combination Index (CI) | Conclusion |
|-----------|--------------|---------------------|------------|-------------------------|------------------------------------|-----------------------|------------|
| AMO-1     | Experiment 1 | 1.2                 | −0.2       | 1.0                     | 1.7                                | <<0.1 *               | synergy    |
|           | Experiment 2 | 0.7                 | 0.3        | 1.0                     | 1.4                                | <<0.1 *               | synergy    |
|           | Experiment 3 | 0.8                 | 0.2        | 1.0                     | 1.3                                | <<0.1 *               | synergy    |
|           | AVERAGE      | 0.9                 | 0.1        | 1.0                     | 1.5                                | —                     | —          |

Table 4c represents the normalization of the data, where the theoretical combination is set as 1 (100%) and includes the CI Chou et al. calculations using the methodology described above within Example 4.

Table 4c differs from Tables 4a and 4b. Table 4c is based upon different raw data points than shown in Table 4a, as the concentrations chosen in Table 4c are closer to the $EC_{50}$ of the antibody (raw data not shown).

1. Determination of Synergism 1.2 Clarke et al. Synergism

Where one drug has low activity, as in here where Lenalidomide alone has low cytotoxicity against AMO-1 cells, synergy can also be determined by statistical evidence that the combination is significantly different from the inhibitory drug alone. See Clarke et al., Issues in experimental design and endpoint analysis in the study of experimental cytotoxic agents in vivo in breast cancer and other models, Breast Cancer Research and Treatment 46:255-278 (1997), which is incorporated by reference in its entirety. Here both Chou et al. as shown above and the methods of Clarke et al. were used in the determination of synergism.

The data is analysed in the following way:

Antagonistic (AB)/C<(A/C)×(B/C)

Additive (AB)/C=(A/C)×(B/C)

Synergistic (AB)/C>(A/C)×(B/C)

where A is the treatment with LEN alone; B is the treatment with MOR202 alone; C is response to the treatment vehicle; AB is combination of treatments A and B.

TABLE 5

The raw data values shown in this table are the same as those shown in Table 3a, as they come from the same three experiments, where both effector and AMO-1 cells were treated with Lenalidomide prior to treatment with MOR202 and the single and combination doses of 10 µM LEN and 15 µg/ml of MOR03207 and MOR202 were used. The only difference is that the data is analyzed using Clarke et al. instead of Chou et al.

|                              | Experiment 1 | Experiment 2 | Experiment 3 |
|------------------------------|--------------|--------------|--------------|
| A: LEN alone                 | 15.41        | 8.44         | 22.38        |
| B: MOR202 alone              | 23.69        | 22.53        | 49.56        |
| C: control                   | 11.07        | 8.45         | 26.43        |
| AB: combination of LEN and MOR202 | 35.98   | 29.09        | 80.39        |
| (AB)/C                       | 3.25         | 3.44         | 3.04         |
| (A/C) × (B/C)                | 2.98         | 2.66         | 1.59         |

TABLE 5-continued

The raw data values shown in this table are the same as those shown in Table 3a, as they come from the same three experiments, where both effector and AMO-1 cells were treated with Lenalidomide prior to treatment with MOR202 and the single and combination doses of 10 µM LEN and 15 µg/ml of MOR03207 and MOR202 were used. The only difference is that the data is analyzed using Clarke et al. instead of Chou et al.

|   | Experiment 1 | Experiment 2 | Experiment 3 |
|---|--------------|--------------|--------------|

A = response to treatment with LEN alone
B = response to treatment with MOR202 alone
C = response to treatment with control
AB = combination of treatments A and B
The values of A, B, C and AB represent % cell killing.

In each experiment (AB)/C is greater than (A/C)×(B/C), showing clear synergy.

TABLE 6

The raw data values shown in this table are the same as those shown in Table 4a, as they come from the same three experiments, where only the effector cells were treated with Lenalidomide prior to treatment with MOR202 and the single and combination doses of 10 µM LEN and 15 µg/ml of MOR03207 and MOR202 were used. The only difference is that the data is analyzed using Clarke et al. instead of Chou et al.

|                     | Experiment 1 | Experiment 2 | Experiment 3 |
|---------------------|--------------|--------------|--------------|
| A: LEN alone        | 15.33        | 12.98        | 17.93        |
| B: MOR202 alone     | 23.09        | 21.08        | 48.28        |
| C: Control          | 15.97        | 11.45        | 15.77        |
| AB: combination of  | 23.46        | 25.75        | 56.49        |

TABLE 6-continued

The raw data values shown in this table are the same as those shown in Table 4a, as they come from the same three experiments, where only the effector cells were treated with Lenalidomide prior to treatment with MOR202 and the single and combination doses of 10 µM LEN and 15 µg/ml of MOR03207 and MOR202 were used. The only difference is that the data is analyzed using Clarke et al. instead of Chou et al.

|  | Experiment 1 | Experiment 2 | Experiment 3 |
|---|---|---|---|
| LEN and MOR202 |  |  |  |
| (AB)/C | 1.47 | 2.25 | 3.58 |
| (A/C) × (B/C) | 1.39 | 2.09 | 3.48 |

A = response to treatment with LEN alone
B = response to treatment with MOR202 alone
C = response to treatment with control
AB = combination of treatments A and B In each experiment (AB)/C is greater than (A/C)×(B/C), showing clear synergy.

Results

Applying the analysis of Clarke et al., LEN synergistically enhanced MOR202 ADCC activity in AMO-1 cells in all 6 experiments. Applying the analysis of Chou et al., LEN synergistically enhanced MOR202 ADCC activity in AMO-1 cells in 6 out of 6 experiments. This enhancement of activity was identified to be by several mechanisms including direct cytotoxicity, activation of effector cells and upregulation of CD38 expression levels on MM cells.

Experiments according to example 4 are also performed with other antibodies specific for CD38, for example, the "Ref mAB5" antibody.

Example 5

Inhibition of Proliferation of NCI-H929 Cells Using Lenalidomide Alone

The cytotoxicity of Lenalidomide was tested in NCI-H929 using the methods described in Example 3. The results are shown in FIG. 2. In summary, challenge with Lenalidomide alone significantly inhibited cell proliferation in NCI-H929 cells.

Example 6

Synergistic Combination of MOR202 and Lenalidomide in NCI-H929 Cells

NCI-H929 cells were selected for testing with the combination of MOR202 and lenalidomide. NCI-H929 cells express higher levels of CD38 than AMO-1 cells, therefore, are representative of certain cells types found in human patients with multiple myeloma or non-Hodgkin's lymphoma.

In total six experiments were performed, using the methods described in Example 4, in order to determine the mediation of ADCC on NCI-H929 cells by the combination of MOR202 and lenalidomide. In three experiments, the PBMCs and NCI-H929 cells were treated with lenalidomide prior to treatment with MOR202, the results are shown in Tables 7a-b and FIG. 6. In three additional experiments only the PBMCs were treated with lenalidomide prior to treatment with MOR202, the results are shown in Tables 8a-b and FIG. 7.

Table 7 Both Effector and NCI-H929 cells were treated with Lenalidomide prior to treatment with MOR202. Single and combination doses of 5 µM LEN and 15 µg/ml of MOR03207 and 0.2 or 0.07 µg/ml MOR202 were used.

The data is presented in the following ways, as a) raw data (% dead cells), and b) normalized specific killing data, where the fractional product combination is set as 1 (100%). Table 7a represents raw data.

TABLE 7a

| NCI-H929 | LEN 5 µM alone | MOR202 alone (0.2* or 0.07 µg/ml) | Combination of LEN (5 µM) and MOR202 (0.2* or 0.07 µg/ml) | DMSO | LEN (0 µM) | MOR03207 (15 µg/ml) + DMSO | MOR03207 (15 µg/ml) |
|---|---|---|---|---|---|---|---|
| Exp. 1 | 38.65 | 30.64* | 60.20* | 18.01 | 18.42 | 18.27 | 17.81 |
| Exp. 2 | 41.92 | 43.08 | 66.62 | 18.77 | 19.92 | 20.26 | 19.20 |
| Exp. 3 | 39.92 | 32.54 | 64.58 | 12.32 | 12.44 | 13.74 | 14.09 |

The units of the values listed are % dead cells. The DMSO, MOR03207, MOR03207+DMSO, LEN0, LEN10 without PBMCs and DMSO without PBMCs are controls.

Table 7b represents normalized data, where the fractional product combination is set as 1 (100%).

TABLE 7b

| NCI-H929 | MOR202 alone (0.2* or 0.07 µg/ml) | LEN 5 µM alone | Combination based upon fractional product concept | Combination of LEN (5 µM) and MOR202 (0.2* or 0.07 µg/ml) | Combination Index (CI) | Conclusion |
|---|---|---|---|---|---|---|
| Exp. 1 | 0.42* | 0.67 | 1.00 | 1.36* | <<0.1 | synergism |
| Exp. 2 | 0.58 | 0.56 | 1.00 | 1.12 | <<0.1 | synergism |
| Exp. 3 | 0.45 | 0.67 | 1.00 | 1.24 | <<0.1 | synergism |
| AVERAGE | 0.48 | 0.83 | 1.00 | 1.24 |  |  |

Figure 6:
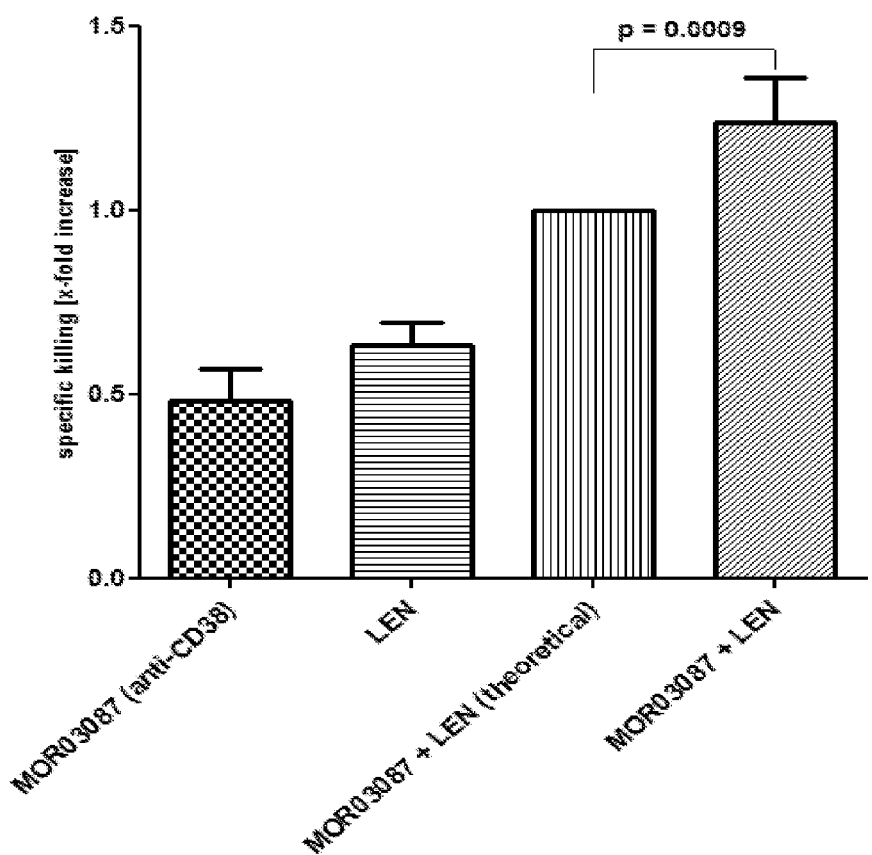
FIG. 6 shows the mediation of ADCC on NCI-H929 cells by the combination of MOR03087 and lenalidomide. The PBMCs and NCI-H929 cells were treated with lenalidomide prior to treatment with MOR03087. Theoretical represent the combination calculated using the fractional product concept of Chou et al. The data shown are the averages from Table 7b.

The fractional product combination is calculated using the following formula 1-[(1-A)*(1-B)]=fpc (%) as described in Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety. Table 7b is based upon the raw data shown in Table 7a. The normalization of the data as shown in Table 7b is calculated as described in Table 3b, by substracting the controls. In Table 7b, where the combination of LEN and MOR202 is greater than the combination based upon the fractional product concept, then clear synergy exists. In addition, Combination Index values were calculated using the methods of Chou et al. as described in Example 4. The averages of the results of Table 7b are shown in FIG. 6.

Table 8 Effector cells only treated with Lenalidomide prior to treatment with MOR202. Single and combination doses of 5 µM LEN and 15 µg/ml of MOR03207 and 0.2* or 0.07 µg/m MOR202 were used.

The data is presented in the following ways, as a) raw data (% dead cells), and b) normalized specific killing data, where the fractional product combination is set as 1 (100%). Table 8a represents raw data.

Example 5, therefore, the fractional product concept is utilized. The fractional product concept was described in Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety. There Chou et al. states: If A and B each inhibits 60%, then it is oversimplification to say that the additive effect is 84% inhibition. Based on the reasoning by Webb (1963), this type of problem can be solved by (1-0.6)(1-0.6)=0.16, 1-0.16=0.84. Chou and Talalay (1984) called it the fractional product method. This method will never lead to a combination effect exceeding 100% inhibition. Chou and Talalay (1984), however, have also proved that this method has limited validity because it takes into account the potency (e.g., fractional inhibition) but ignores the shape of the dose-effect curve (e.g., hyperbolic or sigmoidal). The importance of the "shape" in a dose-effect analysis is shown in FIG. 1. Chou and Talalay (1984) indicated that Webb's method is valid only when both drugs have hyperbolic curves (i.e., in simple Michaelis-Menten kinetics when dose-effect curves are hyperbolic, i.e., m=1 in the median-effect plot) and is not valid when m does not equal 1, such as sigmoidal (m>1) or flat TABLE 8a

| NCI-H929 | LEN 5 µM alone | MOR202 alone (0.2* or 0.07 µg/ml) | Combination of LEN (5 µM) and MOR202 (0.2* or 0.07 µg/ml) | DMSO | LEN (0 µM) | MOR03207 (15 µg/ml) + DMSO | MOR03207 (15 µg/ml) |
|---|---|---|---|---|---|---|---|
| Exp. 1 | 17.50 | 26.60* | 29.11* | 18.36 | 17.56 | 19.52 | 17.07 |
| Exp. 2 | 25.72 | 47.00 | 51.23 | 22.55 | 24.90 | 24.16 | 23.19 |
| Exp. 3 | 26.27 | 53.74 | 67.99 | 25.29 | 25.16 | 24.43 | 27.10 |

The units of the values listed are % dead cells. The DMSO, MOR03207, MOR03207+DMSO, LEN0, LEN10 without PBMCs and DMSO without PBMCs are controls.

Table 8b represents the normalized data, where the fractional product combination is set as 1 (100%).

sigmoidal (m<1) curves. Furthermore, Webb's method is valid when the effects of two drugs are mutually nonexclusive (e.g., totally independent) and is not valid for mutually exclusive (e.g., similar mechanisms or modes of actions, as assumed for the classic isobologram, see below).

TABLE 8b

| NCI-H929 | MOR202 alone (0.2* or 0.07 µg/ml) | LEN 5 µM alone | Combination based upon fractional product concept | Combination of LEN (5 µM) and MOR202 (0.2* or 0.07 µg/ml) | Combination Index (CI) | Conclusion |
|---|---|---|---|---|---|---|
| Exp. 1 | 1.09* | −0.10 | 1.00 | 1.10* | 0.07 | synergism |
| Exp. 2 | 0.91 | 0.12 | 1.00 | 1.03 | 0.81 | synergism |
| Exp. 3 | 0.97 | 0.04 | 1.00 | 1.59 | <<0.1 | synergism |
| AVERAGE | 0.99 | 0.02 | 1.00 | 1.24 | | |

Figure 7:
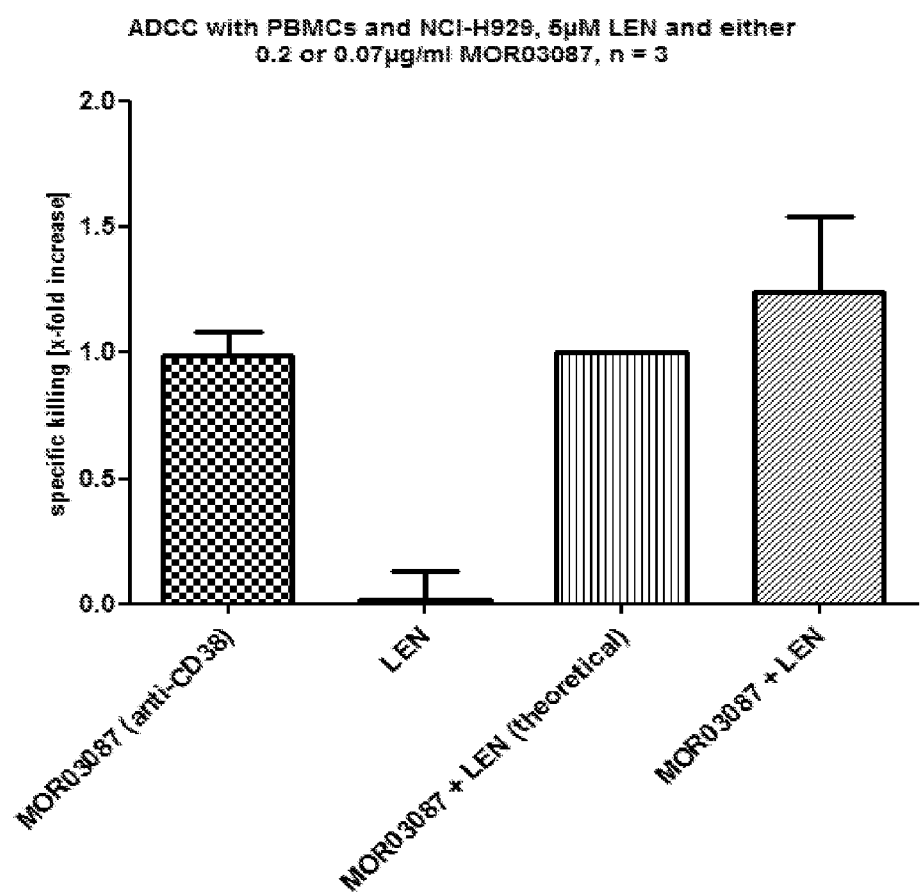
FIG. 7 shows the mediation of ADCC on NCI-H929 cells by the combination of MOR03087 and lenalidomide. Only the PBMCs were treated with lenalidomide prior to treatment with MOR03087. Theoretical represent the combination calculated using the fractional product concept of Chou et al. The data shown are the averages from Table 8b.

Table 8b is based upon the raw data shown in Table 8a. The normalization of the data as shown in Table 8a is calculated as described in Table 3b, by substracting the controls. In Table 8b, where the combination of LEN and MOR202 is greater than the combination based upon the fractional product concept, then clear synergy exists. In addition, Combination Index values were calculated using the methods of Chou et al. as described in Example 4. The averages of the results of Table 8b are shown in FIG. 7.

Determination of Synergism 1.3 Fractional Product Concept

The evaluation of the data in this example differs from that used in the analysis of the effect of the combination of MOR202 and LEN on AMO-1 cells in Example 4. Here NCI-H929 cells are tested and LEN alone has a significant effect on the proliferation of NCI-H929 cells as shown in Clarke et al. was not utilized as Clarke is most suitable when one monotherapy has a low effect.

See FIG. 12, the best fit curve was determined by removing the data points a) where the concentration of MOR202 was too low to have any effect and b) where the concentration was near saturation. At the appropriate date point, approx. 80% cell killing, the CI value is less than 1, supporting clear synergy.

Results

Applying the analysis of the Fractional Product Concept, LEN synergistically enhanced MOR202 activity in NCI-H929 cells in 6 out of 6 experiments. Applying the analysis of Chou et al., LEN synergistically enhanced MOR202 activity in NCI-H929 cells in 6 out of 6 experiments. See Tables 7a-b, and 8a-b.

Example 7

MOR202 and LEN Alone and in Combination in NCI-H929 Bone Lysis SCID Mouse MM Model

Materials

Lenalidomide (SYNthesis med chem; Shanghai, China; Lot no: ZHM-066-051). MOR202 (MorphoSys AG, Lot 100706-5KLE18). Vehicle control: Ora-Plus: Ora-Sweet SF (Paddock Laboratories, Minneapolis, Minn., USA, Lot no. 9499528). SCID Mice (University of Adelaide, Waite Campus, Urrbaraie, SA, Australia, Strain C.B.-17-Igh-1$^b$-Prkdc$^s_{cid}$). NCI-H929 human multiple myeloma cells (see Table 1). RPMI 1640 cell culture medium, Foetal Bovine Serum (FBS), Mercaptoethanol, Hank's Balanced Salt Solution (HBSS) and penicillin-streptomycin from Invitrogen Australia (Mt Waverley, VIC, Australia); and Trypan Blue and glucose from Sigma-Aldrich (Castle Hill, NSW, Australia).

Methods

63 SCID mice were inoculated on Day (−7) orthotopically into the right tibia with $2.5 \times 10^6$ NCI-H929 MM cells (in 5 µL) in order to induce bone lysis. Three days post inoculation (Day −4) 60 of the SCID mice were randomized by body weight into the groups shown in Table 13, 10 mice per group. The dosing regimen is provided in Table 9. Lenalidomide (Groups A and D) and Vehicle Control (Group C) treatments started on Day (−1). MOR202 treatments (Groups B and D) started on Day 0. Treatment continued for 6 weeks.

TABLE 9

Dosing regimen and Groups

| Group | Compound | Treatment | Schedule |
|---|---|---|---|
| A | Lenalidomide | 50 mg/kg, p.o. in 10 mL/kg | once daily for 6 weeks |
| B | MOR202 | 3 mg/kg, i.p., in 10 mL/kg | 3 times weekly for 6 weeks |
| C | Vehicle Control (Ora-Plus:Ora-Sweet SF (1:1, w/w)) | 10 mL/kg, p.o. | once daily for 6 weeks |
| D | Lenalidomide/ MOR202 Combination | 50 mg/kg, p.o. in 10 mL/kg 3 mg/kg, i.p., in 10 mL/kg | once daily for 6 weeks 3 times weekly for 6 weeks |

Figure 19:
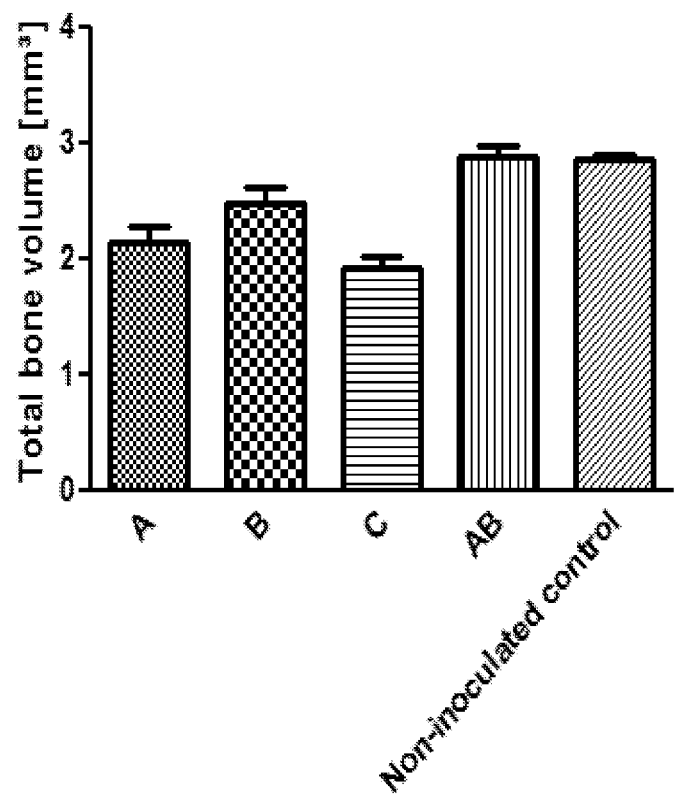
FIG. 19 shows the MicroCT Scan mean total bone volume of each of the study groups described in Example 7, where the results are shown in Table 11.

MicroCT Scan was used to assess bone lysis and included a 3-dimensional analysis comprising Total Bone Volume (TBV), Trabecular Bone Volume (Tb.BV), Trabecular Pattern Factor (Tb.Pf) and Structure Model Index (SMI). Table 10 defines each of these parameters. The results of each of the MicroCT Scan parameters are shown in Table 11. The Total Bone Volume (TBV) results are shown in FIG. 19.

TABLE 10

MicroCT Scan parameters

| Parameters: | Definitions: |
|---|---|
| Total Bone Volume (mm3) | Total cortical and trabecular bone volume within the volume of interest (cross-section). |
| Trabecular Bone Volume | Trabecular bone volume within the volume of interest (cross-section). |
| *Trabecular Pattern Factor (Tb.Pf) | Fragmentation index; An inverse index of connectivity with specific application to the trabecular bone. A lower Tb.Pf signifies better connected trabecular lattices while higher Tb.Pf means a more disconnected trabecular structure (I.e. more bone lysis). |
| ** Structure Model Index (SMI) | An indicator of the relative prevalence of rods and plates in a 3D structure such as the trabecular bone. This parameter is important in osteolysis of the bone which is characterised by a transition from plate-like (normal) to rod-like (degradation) structures. An ideal plate, cylinder and sphere have SMI values of 0, 3 and 4 respectively. The higher the value, the more damage there is. |

TABLE 11

Results of the MicroCT Scan: Total Bone Volume (TBV), Trabecular Bone Volume (Tb. BV), Trabecular Pattern Factor (Tb. Pf) and Structure Model Index (SMI).

| Group | Treatment | Mouse ID | Total Bone Volume (TBV) mm$^{-3}$ | Trabecular Bone Volume (Tb. BV) mm$^{-2}$ | Trabecular Pattern Factor (Tb. Pf) mm$^{-1}$ | Structure Model Index (SMI) |
|---|---|---|---|---|---|---|
| Control | Non inoculated reference tibia* | 38045 | 2.748 | 0.244 | 15.354 | 1.756 |
| | | 38596 | 2.839 | 0.295 | 12.373 | 1.542 |
| | | 39565 | 2.930 | 0.314 | 14.703 | 1.847 |
| | | 38325 | 2.964 | 0.309 | 13.538 | 1.653 |
| | | 33746 | 2.751 | 0.293 | 13.270 | 1.624 |
| | | 38770 | 2.567 | 0.307 | 13.025 | 1.645 |
| | | 37966 | 2.967 | 0.410 | 12.125 | 1.557 |
| | | 38604 | 3.087 | 0.327 | 11.902 | 1.658 |
| | | 38023 | 2.775 | 0.270 | 18.005 | 1.889 |
| | | 38594 | 2.830 | 0.311 | 13.293 | 1.589 |
| | | Mean | 2.846 | 0.308 | 13.759 | 1.676 |
| | | SEM | 0.047 | 0.014 | 0.583 | 0.037 |
| A | Lenalidomide, 50 mg/kg | 33150 | 1.604 | 0.107 | 24.329 | 2.679 |
| | | 38027 | 1.742 | 0.100 | 23.561 | 2.667 |
| | | 38314 | 2.506 | 0.256 | 22.893 | 2.335 |

TABLE 11-continued

Results of the MicroCT Scan: Total Bone Volume (TBV), Trabecular Bone Volume
(Tb. BV), Trabecular Pattern Factor (Tb. Pf) and Structure Model Index (SMI).

| Group | Treatment | Mouse ID | Total Bone Volume (TBV) $mm^{-3}$ | Trabecular Bone Volume (Tb. BV) $mm^{-2}$ | Trabecular Pattern Factor (Tb. Pf) $mm^{-1}$ | Structure Model Index (SMI) |
|---|---|---|---|---|---|---|
| | | 38446 | 2.466 | 0.213 | 28.280 | 2.560 |
| | | 38562 | 2.688 | 0.385 | 22.213 | 2.086 |
| | | 38626 | 2.869 | 0.293 | 30.739 | 2.619 |
| | | 38748 | 1.786 | 0.114 | 24.016 | 2.562 |
| | | 39192 | 1.988 | 0.081 | 29.454 | 2.592 |
| | | 39364 | 1.741 | 0.155 | 24.205 | 2.547 |
| | | 39512 | 2.007 | 0.219 | 38.360 | 3.125 |
| | | Mean | 2.140 | 0.192 | 26.805 | 2.577 |
| | | SEM | 0.143 | 0.031 | 1.584 | 0.083 |
| B | MOR03087, 3 mg/kg | 32094 | 2.233 | 0.190 | 27.049 | 2.386 |
| | | 32548 | 2.893 | 0.310 | 15.631 | 1.818 |
| | | 33564 | 2.760 | 0.356 | 27.631 | 2.423 |
| | | 38016 | 1.635 | 0.118 | 27.523 | 2.450 |
| | | 38023 | 2.681 | 0.248 | 17.887 | 1.860 |
| | | 38510 | 1.838 | 0.260 | 21.405 | 2.461 |
| | | 38599 | 2.884 | 0.482 | 26.345 | 2.558 |
| | | 39086 | 3.068 | 0.566 | 20.327 | 2.247 |
| | | 39666 | 2.547 | 0.416 | 25.843 | 2.318 |
| | | 39715 | 2.135 | 0.284 | 22.402 | 2.275 |
| | | Mean | 2.467 | 0.323 | 23.204 | 2.280 |
| | | SEM | 0.153 | 0.043 | 1.365 | 0.079 |
| C | Vehicle Control (Ora Plus:Ora Sweet SF (1:1, w/w)) | 33090 | 1.821 | 0.159 | 26.537 | 2.714 |
| | | 33131 | 1.863 | 0.132 | 28.429 | 2.681 |
| | | 33746 | 1.577 | 0.130 | 29.171 | 2.652 |
| | | 37966 | 1.865 | 0.234 | 18.276 | 2.327 |
| | | 38325 | 2.030 | 0.096 | 30.839 | 2.591 |
| | | 38596 | 1.870 | 0.154 | 33.079 | 2.783 |
| | | 38604 | 1.904 | 0.232 | 23.234 | 2.607 |
| | | 38770 | 2.461 | 0.210 | 19.149 | 2.137 |
| | | 39426 | 1.556 | 0.184 | 21.846 | 2.348 |
| | | 39565 | 2.235 | 0.256 | 24.545 | 2.365 |
| | | Mean | 1.918 | 0.179 | 25.510 | 2.521 |
| | | SEM | 0.087 | 0.017 | 1.567 | 0.067 |
| AB | Lenalidomide, 50 mg/kg/ MOR03087, 3 mg/kg | 32695 | 2.471 | 0.168 | 21.323 | 2.028 |
| | | 37854 | 2.527 | 0.265 | 15.938 | 1.758 |
| | | 38276 | 3.212 | 0.220 | 20.046 | 2.197 |
| | | 38550 | 2.833 | 0.186 | 17.907 | 1.892 |
| | | 38594 | 3.044 | 0.268 | 16.530 | 1.787 |
| | | 38994 | 2.896 | 0.408 | 14.633 | 1.683 |
| | | 39256 | 2.308 | 0.304 | 24.513 | 2.280 |
| | | 39555 | 3.227 | 0.215 | 19.753 | 2.497 |
| | | 39677 | 3.205 | 0.548 | 12.313 | 1.799 |
| | | 39750 | 2.961 | 0.281 | 14.981 | 1.752 |
| | | Mean | 2.868 | 0.286 | 17.794 | 1.967 |
| | | SEM | 0.105 | 0.036 | 1.152 | 0.086 |

The analysis of each parameter for synergistic activity was performed according to theorem of Clarke et al. Table 12 shows the calculations done to determine synergy of the combination of MOR202 and lenalidomide.

TABLE 12

| When POSITIVE EFFECT has a HIGH value: | When POSITIVE EFFECT has a LOW value: |
|---|---|
| Antagonistic = (AB)/C < (A/C) × (B/C) | Antagonistic = (AB)/C > (A/C) × (B/C) |
| Additive = (AB)/C = (A/C) × (B/C) | Additive = (AB)/C = (A/C) × (B/C) |
| Synergistic = (AB)/C > (A/C) × (B/C) | Synergistic = (AB)/C < (A/C) × (B/C) |

| | Total BV | Trabecular BV | Trabecular pattern factor | Structural Model Index |
|---|---|---|---|---|
| A | 2.14 | 0.192 | 26.805 | 2.577 |
| B | 2.467 | 0.323 | 23.204 | 2.28 |
| C | 1.918 | 0.179 | 25.51 | 2.521 |
| AB | 2.868 | 0.286 | 17.794 | 1.967 |
| (AB)/C | 1.495307612 | 1.597765363 | 0.69753038 | 0.780245934 |
| | is bigger than | is less than | is less than | is less than |
| (A/C) × (B/C) | 1.44 | 1.94 | 0.96 | 0.92 |

A = response to treatment LEN 50 mg/kg
B = response to treatment MOR202 3 mg/kg
C = response to treatment vehicle
AB = combination of treatments 1 and 2

The numeric values shown in Table 12 are taken directly from the averages shown in Table 11 for each of the parameters in each of the Groups. The Groups described as A, B, C and AB are the same treatment groups in both Tables 9, 11 and 12.

In Total Bone Volume (AB)/C is greater than (A/C) X (B/C) showing clear synergism. In Trabecular pattern factor and Structural Model Index, as described in Table 10, a lower value represents less bone lysis (efficacy in treatment), therefore, (AB)/C less than (A/C) X (B/C), shows clear synergism in both parameters.

Results

The inoculation of NCI-H929 multiple myeloma cells induced significant bone lysis in the tibiae of female SCID mice in this study, as indicated by the measurement of bone lysis through microCT scanning. The degree of bone lysis was significantly decreased in the tibia of mice treated with the combination of MOR202 and lenalidomide as shown by microCT scanning. In each of the parameters of MicroCT Scan: Total Bone Volume (TBV), Trabecular Bone Volume (Tb.BV), Trabecular Pattern Factor (Tb.Pf) and Structure Model Index (SMI) the combination of MOR202 and lenalidomide (Group AB) showed clear synergy in the reduction of bone lysis caused by the NCI-H929 multiple myeloma cells.

When the values in Table 11 are adjusted, so that the Control Group (Non-inoculated Contralateral Tibia without Tumour) is considered 0% bone lysis, and Group C (Vehicle Control (0.9% Sodium Chloride Injection) is considered 100% bone lysis, then MOR202 alone reduced bone lysis dose-dependently by up to 55% at 12 mg/kg compared to vehicle control. LEN alone at 50 mg/kg inhibited bone lysis by 20%. The combination of 3 mg/kg MOR202 and 50 mg/kg LEN completely abolished bone lysis. These findings support a synergistic effect of combination therapy. In addition, there was a reduction (>90%) of M-protein serum levels in the combination group, indicating a significant decrease of tumor load.

Example 8

MOR202 and Lenalidomide Alone and in Combination Against Human Non-Hodgkin RAMOS Tumor in Female SCID Mice, Survival Model Materials Cyclophosphamide (Fluke, Buchs Switzerland, Lot. No. 07551661). Lenalidomide (SYNthesis Med Chem; Shanghai, China; Lot. #ZHM-066-051). MOR202 (MorphoSys AG, Lot 100706-5KLE18). Vehicle Control: Ora-Plus:Ora-Sweet SF, 1:1, v/v (SYNthesis Med Chem, Shanghai, China). SCID Mice (University of Adelaide, Waite Campus, Urrbaraie, SA, Australia, Strain C.B.-17-Igh-1$^b$-Prkdc$^{scid}$).

RAMOS cells (Oncodesign, Dijon Cedex, France) were cultivated in RPMI1640+20% heat inactivated alternate source FBS+1% Glutamax (Medium #2). Reagents for culture of RAMOS non-Hodgkin lymphoma cells were obtained from the following suppliers: RPMI 1640 cell culture medium, FBS, Glutamax, HEPES, sodium pyruvate, HBSS, and penicillin-streptomycin from Invitrogen Australia (Mt Waverley, VIC, Australia); and Trypan Blue and glucose from Sigma-Aldrich (Castle Hill, NSW, Australia).

Methods

Sixty-eight female SCID mice were pre-treated with Cyclophosphamide (75 mg/kg, i.p., twice daily) for two days prior to RAMOS cell inoculation (Day −5 and −4). On the day of inoculation (Day −3), all mice were inoculated with 1×10$^6$ RAMOS cells each intravenously into the tail vein. Sixty-four of the mice were randomised by body weight into eight groups of eight. The dosing regimen for each group is shown in Table 13.

TABLE 13

Dosing regimen

| Group | Compound | Treatment | Intended Schedule | Actual Schedule |
|---|---|---|---|---|
| A | Lenalidomide | 50 mg/kg, p.o., in 10 mL/kg | Once daily (Day 0-20) | Day 0-20 |
| B | MOR03087 | 1 mg/kg, i.v., in 10 mL/kg | Twice weekly (Day 0, 4, 7, 11, 14 and 18) | Twice weekly (Day 0, 4, 7, 11, 14 and 18) |
| C | Vehicle Control (Ora-Plus:Ora-Sweet, 1:1, v/v) | p.o., 10 mL/kg | Once daily (Day 0-20) | Day 0-18 |
| AB | Lenalidomide/ MOR03087 | 100/1 mg/kg, p.o./i.v., in 10 mL/kg | Once daily/twice weekly (as above) | Day 0-13 and 16-20/ Day 0, 4, 7, 11, 14 and 18 |

The study continued for 98 days and the measured endpoint was survival. The results of each Group are shown in Table 14.

TABLE 14

Survival Number and time period for each group

| | Day of death (post-inoculation) | | | | % ILS (based on median | Number of mice alive at study |
|---|---|---|---|---|---|---|
| | Median | Range | Mean | 95% CI | death day) | termination (day 98) |
| A: LEN 100 mg/kg | 22 | 18-23 | 21.4 | 19.8-23.0 | 10 | 0/7 |
| B: MOR202 1 mg/kg | 51 | 35-65 | 49.6 | 41.9-57.3 | 155 | 0/8 |
| C: Vehicle control | 20 | 18-21 | 19.8 | 18.7-20.8 | X | 0/8 |
| AB: Combo LEN/MOR | 65 | 32-98 | 66.5 | 41.9-91.2 | 225 | 3/8 |

Analysis for synergistic activity was performed according to theorem of Clarke et al., as described in Example 4. Table 15 shows the calculations done in the determination of synergy of the combination of MOR202 and lenalidomide.

TABLE 15

| When POSITIVE EFFECT has a HIGH value: | When POSITIVE EFFECT has a LOW value: |
|---|---|
| Antagonistic = (AB)/C < (A/C) × (B/C) | Antagonistic = (AB)/C > (A/C) × (B/C) |
| Additive = (AB)/C = (A/C) × (B/C) | Additive = (AB)/C = (A/C) × (B/C) |
| Synergistic = (AB)/C > (A/C) × (B/C) | Synergistic = (AB)/C < (A/C) × (B/C) |

| | Median survival |
|---|---|
| A | 22 |
| B | 51 |
| C | 20 |
| AB | 65 |
| (AB)/C | 3.25 |

| | is bigger than |
|---|---|
| (A/C) × (B/C) | 2.805 |

A = response to treatment with LEN 100 mg/kg
B = response to treatment with MOR202 1 mg/kg
C = response to treatment vehicle
AB = combination of treatments A and B The numeric values shown in Table 15 are taken directly from the median survival days shown in Table 14 for each of the Groups. The Groups described as A, B, C and AB are the same treatment groups in Tables 13-15.

The inoculation with RAMOS cells was lethal within a median time of 20 days in the control group. The combination of MOR202 and lenalidomide, however, showed clear synergy in the increase in median survival days.

Example 9

Bortezomib Alone Inhibits Proliferation of Various Multiple Myeloma Cell Lines

Figure 8:
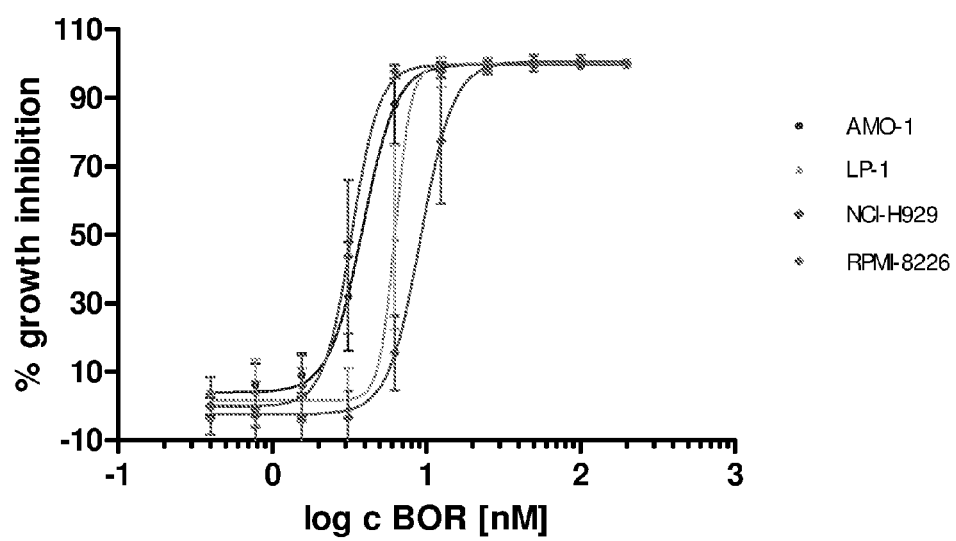
FIG. 8 shows the growth inhibition of various multiple myeloma cell lines caused by bortezomib alone. The IC50 on AMO-1 cells was 3.9 nM. The IC50 on LP-1 cells was 6.1 nM. The IC50 on NCI-H929 cells was 3.3 nM. The IC50 on RPMI-8226 cells was 9.0 nM.

The inhibitory effect of Bortezomib on proliferation of multiple myeloma cells was analysed for multiple cell lines. Increasing amounts of Bortezomib (Velcade®, Lot: No.: #9AZSY00) were applied to AMO-1, LP-1, NCI-H929 and RPMI-8226 cells and incubated for 24 h, 48 h and 72 h. After incubation, period plates were analyzed for cell proliferation in a quantitative colorimietric XTT-based assay using the cell proliferation kit II (ROCHE, Cell Proliferation Kit II, Cat. No.: 11465015001). For subsequent measurement, plates were subjected to Tecan Genios Reader and absorbance at 492 nm was detected. Cell proliferation of all tested cell lines was inhibited by Bortezomib with an $IC_{50}$ concentration of 3.9 nM for AMO-1 cells, 6.1 nM for LP-1 cells, 3.3 nM for NCI-H929 cells and 9.0 nM for RPMI-8226 cells respectively, as shown in FIG. 8.

Example 10

ADCC Using Combination of MOR202 and Bortezomib

Figure 9:
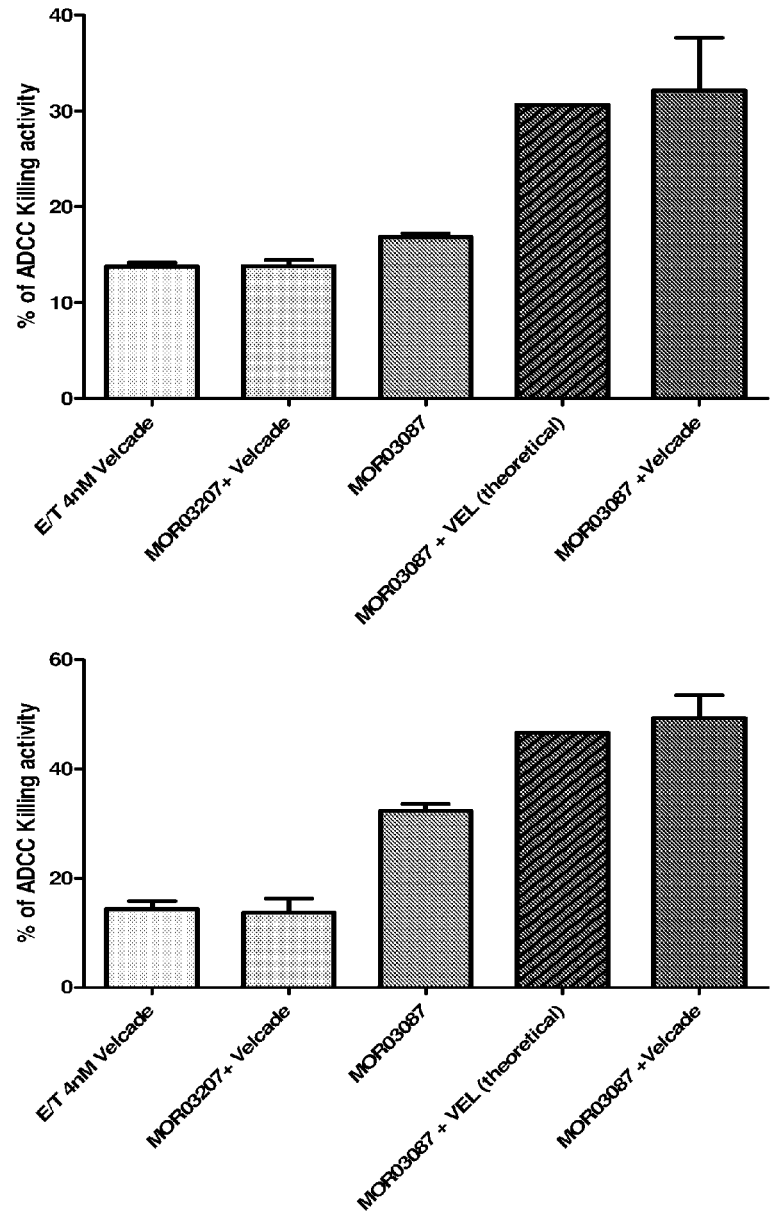
FIG. 9 shows the mediation of ADCC on NCI-H929 cells by the combination of MOR03087 at 15 μg/ml and Velcade® (bortezomib). The two charts represent two different donors.

Using the methods described in Example 4, the ADCC effect of combining bortezomib and MOR202 was analyzed. Here, the target cells were treated with bortezomib prior to the treatment with MOR202. Both target cells, NCI-H929 and LP-1 cells were tested. The results are shown in FIGS. 9 and 10. The enhancement in MOR202 activity by bortezomib was mediated through a direct cytotoxic effect on MM cells.

Example 11

MOR202 and BOR Alone and in Combination in Human Multiple Myeloma NCI-H929 Bone Lysis SCID Mouse Model Materials Bortezomib (SYNthesis med chem., Shanghai, China, Lot no. #ZHM-066-054). Bortezomib was formulated in sterile 0.9% Sodium Chloride solution for dosing. MOR202 (MorphoSys AG, Lot 100706-5KLE18). Vehicle control: 0.9% Sodium Chloride Injection. SCID Mice (University of Adelaide, Waite Campus, Urrbaraie, SA, Australia, Strain C.B.-17-Igh-$1^b$-Prkdc$^{scid}$).

Methods

63 SCID mice were inoculated on Day (−7) intra-tibially with $2.5 \times 10^6$ NCI-H929 MM cells in order to induce bone lysis. Three days post inoculation (Day −4) 60 of the SCID mice were randomized by body weight into the groups shown in Table 16, 10 mice per group. The dosing regimen is provided in Table 16. Bortezomib (Groups A and AB) and Vehicle Control (Group C) treatments started on Day (−1). MOR202 treatments (Groups B and AB) started on Day 0. Treatment continued for 6 weeks.

TABLE 16

Dosing regimen and Groups

| Group | Compound | Treatment | Schedule |
|---|---|---|---|
| A | Bortezomib | 0.6 mg/kg, i.p., in 10 mL/kg | twice per week |
| B | MOR202 | 3 mg/kg, i.p., in 10 mL/kg | three times per week |
| C | Vehicle Control (0.9% Sodium Chloride Injection) | i.p., 10 mL/kg | twice per week |
| AB | Bortezomib/ MOR202 | 0.6/3 mg/kg, i.p., in 10 mL/kg | twice/three times per week, on alternate days |

Figure 20:
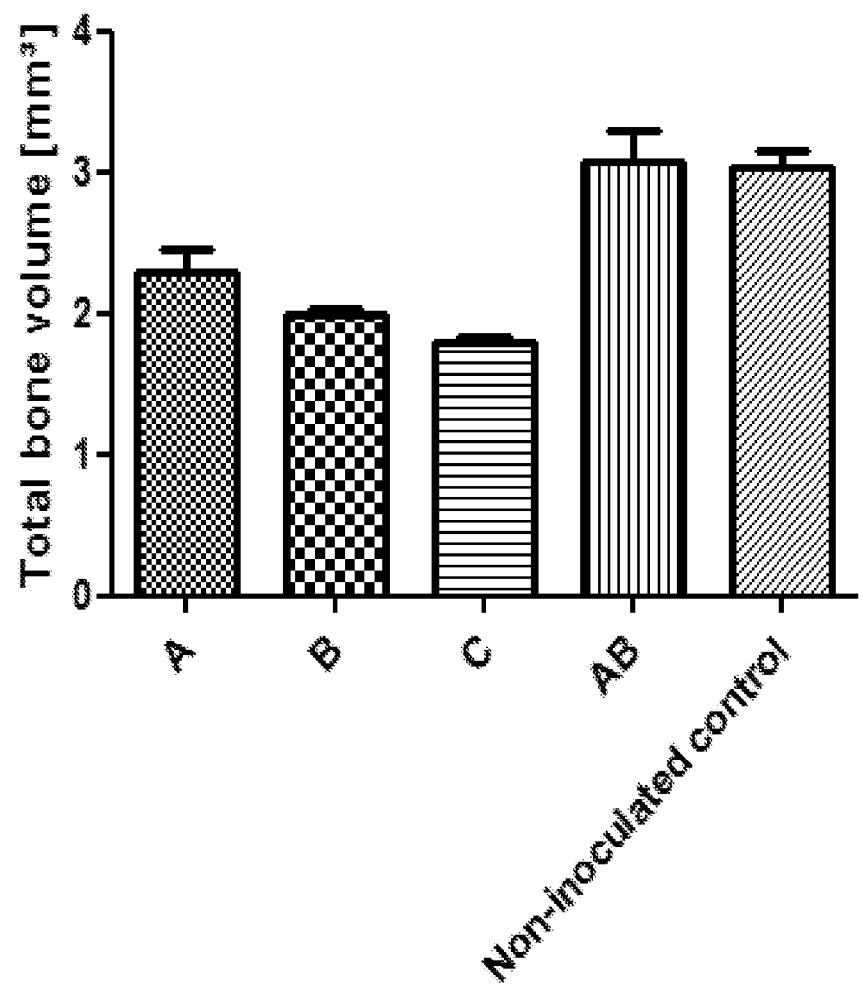
FIG. 20 shows the MicroCT Scan mean total bone volume of each of the study groups described in Example 11, where the results are shown in Table 17.

MicroCT Scan was used to assess bone lysis and included a 3-dimensional analysis comprising Total Bone Volume (TBV), Trabecular Bone Volume (Tb.BV), Trabecular Pattern Factor (Tb.Pf) and Structure Model Index (SMI). Table 10 above defines each of these parameters. The results of each of the MicroCT Scan parameters are shown in Table 17. The results of the Total Bone Volume (TBV) is shown in FIG. 20.

TABLE 17

Results of the MicroCT Scan: Total Bone Volume (TBV), Trabecular Bone Volume (Tb. BV), Trabecular Pattern Factor (Tb. Pf) and Structure Model Index (SMI).

| Group | Treatment | Mouse ID | Total Bone Volume (TBV) $mm^{-3}$ | Trabecular Bone Volume (Tb. BV) $mm^{-2}$ | Trabecular Pattern Factor (Tb. Pf) $mm^{-1}$ | Structure Model Index (SMI) |
|---|---|---|---|---|---|---|
| Control: Non-inoculated Contralateral Tibia without Tumour | Reference tibia, one mouse from Groups A, B, C and AB) | 115898 | 2.771 | 0.400 | 12.097 | 1.525 |
| | | 116259 | 3.255 | 0.598 | 7.999 | 1.264 |
| | | 109482 | 3.194 | 0.566 | 5.596 | 1.025 |
| | | 107508 | 2.945 | 0.346 | 16.910 | 1.860 |
| | | Average | 3.041 | 0.477 | 10.650 | 1.419 |
| | | SEM | 0.112 | 0.062 | 2.481 | 0.179 |
| A | Bortezomib, 0.6 mg/kg, twice per week, i.p. | 101426 | 2.351 | 0.307 | 25.893 | 2.443 |
| | | 105949 | 2.025 | 0.191 | 26.044 | 2.374 |
| | | 107598 | 3.109 | 0.557 | 16.877 | 2.156 |
| | | 109560 | 3.146 | 0.588 | 23.179 | 2.262 |
| | | 113302 | 1.790 | 0.067 | 32.463 | 2.700 |
| | | 115836 | 1.893 | 0.076 | 33.152 | 2.981 |
| | | 116981 | 2.201 | 0.100 | 34.609 | 3.007 |
| | | 117585 | 1.617 | 0.093 | 31.813 | 2.553 |
| | | 117750 | 2.300 | 0.284 | 27.147 | 2.337 |
| | | 117793 | 2.448 | 0.329 | 23.582 | 2.273 |
| | | Average | 2.288 | 0.259 | 27.476 | 2.509 |
| | | SEM | 0.162 | 0.061 | 1.756 | 0.094 |
| B | MOR202, 3 mg/kg, three times per week, i.p. | 106446 | 1.924 | 0.082 | 27.363 | 2.546 |
| | | 109482 | 1.987 | 0.388 | 19.479 | 2.079 |
| | | 112220 | 2.155 | 0.394 | 21.858 | 2.296 |
| | | 113668 | 1.958 | 0.276 | 23.814 | 2.429 |
| | | 115187 | 2.080 | 0.440 | 16.347 | 1.871 |
| | | 115956 | 2.207 | 0.460 | 19.748 | 2.193 |
| | | 116312 | 1.885 | 0.234 | 25.212 | 2.368 |
| | | 116798 | 1.882 | 0.254 | 21.276 | 2.436 |
| | | 116944 | 1.937 | 0.276 | 24.031 | 2.368 |
| | | 117773 | 1.862 | 0.160 | 25.056 | 2.511 |
| | | Average | 1.988 | 0.296 | 22.418 | 2.310 |
| | | SEM | 0.038 | 0.039 | 1.044 | 0.066 |
| C | Vehicle Control (0.9% Sodium Chloride Injection), twice per week, i.p. | 107097 | 1.619 | 0.248 | 22.779 | 2.246 |
| | | 112122 | 1.608 | 0.178 | 26.514 | 2.505 |
| | | 115971 | 1.637 | 0.241 | 24.603 | 2.485 |
| | | 116259 | 1.880 | 0.369 | 19.334 | 2.176 |
| | | 116585 | 2.060 | 0.179 | 24.120 | 2.369 |
| | | 116779 | 1.624 | 0.190 | 23.909 | 2.417 |
| | | 117054 | 1.782 | 0.131 | 23.000 | 2.541 |
| | | 117110 | 1.838 | 0.281 | 22.602 | 2.312 |
| | | 117242 | 1.919 | 0.281 | 21.162 | 2.193 |
| | | 117375 | 1.899 | 0.283 | 23.455 | 2.338 |
| | | Average | 1.786 | 0.238 | 23.148 | 2.358 |
| | | SEM | 0.050 | 0.022 | 0.615 | 0.041 |
| AB | Bortezomib/ MOR202, 0.6/3 mg/kg, twice/three times per week, i.p. | 107508 | 3.303 | 0.927 | 16.902 | 2.158 |
| | | 112625 | 4.254 | 1.661 | 3.000 | 0.772 |
| | | 113322 | 3.684 | 1.332 | 3.888 | 0.884 |
| | | 116030 | 2.422 | 0.192 | 30.272 | 2.542 |
| | | 116198 | 3.537 | 1.037 | 8.023 | 1.217 |
| | | 116376 | 1.933 | 0.255 | 22.059 | 2.321 |
| | | 116520 | 2.793 | 0.654 | 22.439 | 2.336 |
| | | 117077 | 3.402 | 0.658 | 7.207 | 1.241 |
| | | 117093 | 2.436 | 0.643 | 17.454 | 1.927 |
| | | 117135 | 3.026 | 0.627 | 13.699 | 1.775 |
| | | Average | 3.079 | 0.799 | 14.494 | 1.717 |
| | | SEM | 0.220 | 0.144 | 2.836 | 0.204 |

The Analysis of each parameter for synergistic activity was performed according to theorem of Clarke et al., as described in Example 4. Table 18 shows the calculations done in the determination of synergy of the combination of MOR202 and bortezomib.

TABLE 18

| When POSITIVE EFFECT has a HIGHER value: | When POSITIVE EFFECT has a LOWER value: |
|---|---|
| Antagonistic = (AB)/C < (A/C) × (B/C) | Antagonistic = (AB)/C > (A/C) × (B/C) |
| Additive = (AB)/C = (A/C) × (B/C) | Additive = (AB)/C = (A/C) × (B/C) |
| Synergistic = (AB)/C > (A/C) × (B/C) | Synergistic = (AB)/C < (A/C) × (B/C) |

| Group | Total BV | Trabecular BV | Trabecular pattern factor | Structural Model Index |
|---|---|---|---|---|
| A | 2.288 | 0.259 | 27.476 | 2.509 |
| B | 1.988 | 0.296 | 22.418 | 2.31 |

TABLE 18-continued

| | | | | |
|---|---|---|---|---|
| C | 1.786 | 0.238 | 23.148 | 2.358 |
| AB | 3.079 | 0.799 | 14.494 | 1.717 |
| (AB)/C | 1.723964166 | 3.357142857 | 0.626144807 | 0.728159457 |

| | is bigger than | is bigger than | is less than | is less than |
|---|---|---|---|---|
| (A/C) × (B/C) | 1.425967052 | 1.353435492 | 1.149538246 | 1.042377527 |

A = response to treatment with BOR at 0.6 mg/kg
B = response to treatment with MOR202 at 3 mg/kg
C = response to treatment with vehicle 0.9% Sodium Chloride
AB = combination of treatments A and B The numeric values shown in Table 18 are taken directly from the averages shown in Table 17 for each of the parameters in each of the Groups. The Groups described as A, B, C and AB are the same treatment groups in Tables 16-18.

In Total Bone Volume and Trabecular Bone Volume, (AB)/C is greater than (A/C) X (B/C) showing clear synergism. In Trabecular pattern factor and Structural Model Index, as described in Table 10, a lower value represents less bone lysis (efficacy in treatment), therefore, (AB)/C less than (A/C) X (B/C), supports clear synergism in both parameters.

Results

The inoculation of NCI-H929 multiple myeloma cells induced significant bone lysis in the tibiae of female SCID mice in this study, as indicated by the measurement of bone lysis through microCT scanning. The degree of bone lysis was significantly decreased in the tibia of mice treated with the combination of MOR202 and bortezomib as shown by microCT scanning. In each of the parameters of MicroCT Scan: Total Bone Volume (TBV), Trabecular Bone Volume (Tb.BV), Trabecular Pattern Factor (Tb.Pf) and Structure Model Index (SMI) the combination of MOR202 and bortezomib (Group AB) showed clear synergy in the reduction of bone lysis caused by the NCI-H929 multiple myeloma cells.

When the values in Table 17 are adjusted, so that the Control Group (Non-inoculated Contralateral Tibia without Tumour) is considered 0% bone lysis, and Group C (Vehicle Control (0.9% Sodium Chloride Injection) is considered 100% bone lysis, then MOR202 alone reduced bone lysis dose-dependently by up to 55% at 12 mg/kg compared to vehicle control, BOR alone at 0.6 mg/kg inhibited bone lysis by 40% and the combination of a lower dose of 3 mg/kg MOR202 and 0.6 mg/kg BOR completely abolished bone lysis. These findings support a synergistic effect of combination therapy. In addition, there was a reduction (>90%) of M-protein serum levels in the combination group, indicating a significant decrease of tumor load.

Example 12

MOR202 and Bortezomib Alone and in Combination Against Human Non-Hodgkin RAMOS Tumor in Female SCID Mice, Survival Model Materials Cyclophosphamide (Fluka, Buchs Switzerland, WB10468). Bortezomib (SYNthesis med chem., Shanghai, China, Lot no. #ZHM-066-054). Bortezomib was formulated in sterile 0.9% Sodium Chloride solution for dosing. MOR202 (MorphoSys AG, Lot 100706-5KLE18). Vehicle control: 0.9% Sodium Chloride Injection. SCID Mice (University of Adelaide, Waite Campus, Urrbaraie, SA, Australia, Strain C.B.-17-Igh-1$^b$-Prkdc$^{scid}$).

RAMOS cells (Oncodesign, Dijon Cedex, France) were cultivated in RPMI1640+20% heat inactivated alternate source FBS+1% Glutamax (Medium #2). Reagents for culture of RAMOS non-Hodgkin lymphoma cells were obtained from the following suppliers: RPMI 1640 cell culture medium, FBS, Glutamax, HEPES, sodium pyruvate, HBSS, and penicillin-streptomycin from Invitrogen Australia (Mt Waverley, VIC, Australia); and Trypan Blue and glucose from Sigma-Aldrich (Castle Hill, NSW, Australia).

Methods

Fifty-five female SCID mice were pre-treated with Cyclophosphamide (75 mg/kg, i.p., twice daily) for two days prior to RAMOS cell inoculation (Day −5 and −4). On the day of inoculation (Day −3), all fifty-five mice were inoculated with 1×10$^6$ RAMOS cells each (in 100 μL) intravenously into the tail vein. Forty-eight of the mice were randomised by body weight into six groups of eight. The dosing regimen for each group is shown in Table 19.

TABLE 19

Dosing regimen

| Group | Compound | Treatment | Intended Schedule | Actual Schedule |
|---|---|---|---|---|
| A | Bortezomib | 0.6 mg/kg, i.p., in 10 mL/kg | Day −1, 3, 6, 10, 13 and 17 | Day −1, 3, 6 and 13 |
| B | MOR202 | 1 mg/kg, i.v., in 10 mL/kg | Day 0, 4, 7, 11, 14 and 18 | Day 0, 4, 7, 11, 14 and 18 |
| C | Vehicle Control (0.9% Saline for Injection) | i.p., 10 mL/kg | Day −1, 3, 6, 10, 13 and 17 | Day −1, 3, 6, 13 and 17 |
| AB | Bortezomib/MOR202 | 0.6/1 mg/kg, i.p./i.v., in 10 mL/kg | Day −1, 3, 6, 10, 13 and 17/Day 0, 4, 7, 11, 14 and 18 | Day −1, 3, 6, 13, 17 and 20/ Day 0, 4, 7, 11, 14 and 18 |

The study continued for 98 days and the measured endpoint was survival. The results of each Group are shown in Table 20.

TABLE 20

Survival Number and time period for each group

| | Day of death (post-inoculation) | | | | % ILS (based on median death day) | Number of mice alive at study termination (day 98) |
|---|---|---|---|---|---|---|
| | Median | Range | Mean | 95% CI | | |
| A: BOR 0.6 mg/kg | 19 | 18-20 | 19.1 | 18.4-19.8 | −7 | 0/8 |
| B: MOR202 1 mg/kg | 43.5 | 38-52 | 43.6 | 39.0-48.3 | 112 | 0/8 |
| C: Vehicle control | 20.5 | 20-22 | 20.8 | 20.0-21.5 | X | 0/8 |
| AB: Combo BOR/MOR | 45 | 29-98 | 61.6 | 19.7-103.5 | 120 | 2/5 |

Analysis for synergistic activity was performed according to theorem of Clarke et al. Table 21 shows the calculations done in the determination of synergy of the combination of MOR202 and bortezomib.

TABLE 21

When POSITIVE EFFECT has a HIGHER value:

Antagonistic = (AB)/C < (A/C) × (B/C)

Additive = (AB)/C = (A/C) × (B/C)

Synergistic = (AB)/C > (A/C) × (B/C)

| | Median survival |
|---|---|
| A | 19 |
| B | 43.5 |
| C | 20.5 |

TABLE 21-continued

| | |
|---|---|
| AB | 45 |
| (AB)/C | 2.195121951 |
| | is bigger than |
| (A/C) × (B/C) | 1.966686496 |

A = response to treatment with BOR 0.6 mg/kg
B = response to treatment with MOR202 1 mg/kg
C = response to treatment vehicle 0.9% Sodium Chloride
AB = combination of treatments A and B The numeric values shown in Table 21 are taken directly from the median survival days shown in Table 20 for each of the Groups. The Groups described as A, B, C and AB are the same treatment groups in Tables 19-21.

The inoculation with RAMOS cells was lethal within a median time of 20.5 days in the control group. The combination of MOR202 and bortezomib, however, showed clear synergy in the increase in median survival days. Importantly, with the combination of MOR202 and bortezomib (Group AB), 2 out of 5 mice survived for the duration of the study. This strongly supports a synergistic finding of the combination of MOR202 and bortezomib.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

We claim:

1. A synergistic combination of:
   (i) an antibody specific for CD38 comprising an HCDR1 region of sequence GFTFSSYYMN (SEQ ID NO: 1) or SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNL- RHYYVY (SEQ ID NO: 4), an LCDR2 region of sequence GDSKRPS (SEQ ID NO: 5), and an LCDR3 region of sequence QTYTGGASL (SEQ ID NO: 6) and (ii) (a) thalidomide, lenalidomide, or pomalidomide, or (b) a proteasome inhibitor, for use in the treatment of multiple myeloma and/or non-hodgkins lymphoma.

2. A combination according to claim 1, wherein the antibody comprises a variable heavy chain of the sequence:

```
                                            (SEQ ID NO: 10)
QVQLVESGGGLVQPGGSLRLSCAASGFTFSSYYMNWVRQAPGKGLEWVSG

ISGDPSNTYYADSVKGRFTISRDNSKNTLYLQMNSLRAEDTAVYYCARDL

PLVYTGFAYWGQGTLVTV SS
``` and a variable light chain of the sequence

```
                                            (SEQ ID NO: 11)
DIELTQPPSVSVAPGQTARISCSGDNLRHYYVYWYQQKPGQAPVLVIYGD

SKRPSGIPERFSGSNSGNTATLTISGTQAEDEADYYCQTYTGGASLVFGG

GTKLTVLGQ.
```

3. A combination according to claim 1, wherein the antibody comprises an IgG1 Fc region.

4. A combination according to claim 1, wherein the antibody comprises a modified Fc region, wherein said modification enhances ADCC activity.

5. A combination according to claim 1, wherein said antibody specific for CD38 and said thalidomide, lenalidomide, or pomalidomide, or a proteasome inhibitor, are administered separately.

6. A combination according to claim 1, which is able to reduce bone lysis with an at least two-fold better efficacy than lenalidomide and/or bortezomib alone.

7. A combination according to claim 1, wherein the combination comprises thalidomide.

8. A combination according to claim 1, wherein the combination comprises lenalidomide.

9. A combination according to claim 8, wherein lenalidomide is administered prior to administration of the antibody specific for CD38.

10. A combination according to claim 9, wherein lenalidomide is administered at least 72 hours prior to administration of the antibody specific for CD38.

11. A combination according to claim 8, which is able to mediate killing of CD38-expressing AMO-1 and/or NCI-H929 cells by ADCC in the presence of isolated human PBMCs with an at least two-fold better efficacy than lenalidomide alone.

12. A combination according to claim 1, comprising said antibody specific for CD38 and a proteasome inhibitor.

13. A combination according to claim 12, wherein said proteasome inhibitor is bortezomib.

14. A combination according to claim 13, which is able to mediate killing of CD38-expressing LP-1 and/or NCI-H929 cells by ADCC in the presence of isolated human PBMCs with an at least two-fold better efficacy than bortezomib alone.

15. A synergistic combination of:

an antibody specific for CD38 comprising an HCDR1 region of sequence GFTFSSYYMN (SEQ ID NO: 1), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and (ii) lenalidomide, for use in the treatment of multiple myeloma and/or non-hodgkins lymphoma.

16. A synergistic combination of:

(i) an antibody specific for CD38 comprising an HCDR1 region of sequence GFTFSSYYMN (SEQ ID NO: 1), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and (ii) pomalidomide, for use in the treatment of multiple myeloma and/or non-hodgkins lymphoma.

17. A combination according to claim 1, wherein the combination comprises pomalidomide.

18. A combination according to claim 12, wherein said proteasome inhibitor is carfilzomib.

19. A synergistic combination of:

(i) an antibody specific for CD38 comprising an HCDR1 region of sequence GFTFSSYYMN (SEQ ID NO: 1), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and a thalidomide analog, for use in the treatment of multiple myeloma and/or non-hodgkins lymphoma.

* * * * *